(12) United States Patent
Urban et al.

(10) Patent No.: US 7,541,452 B2
(45) Date of Patent: Jun. 2, 2009

(54) RICE REGULATORY SEQUENCES FOR GENE EXPRESSION IN DEFINED WHEAT TISSUE

(75) Inventors: Martin Urban, Luton (GB); Rebecca Stratford, Cambridge (GB); Kim Hammond-Kosack, Harpenden (GB); Pierre Lecocq, Nandrin (BE); Richard Kemp, Cambridge (GB)

(73) Assignee: Monsanto UK Ltd., Cambridge (GB)

( * ) Notice: Subject to any disclaimer, the term of this patent is extended or adjusted under 35 U.S.C. 154(b) by 0 days.

(21) Appl. No.: 12/080,205

(22) Filed: Apr. 1, 2008

(65) Prior Publication Data

US 2008/0271206 A1    Oct. 30, 2008

Related U.S. Application Data

(62) Division of application No. 10/488,149, filed as application No. PCT/EP02/09533 on Aug. 23, 2002, now Pat. No. 7,375,208.

(30) Foreign Application Priority Data

Aug. 28, 2001   (EP)   .................. 01307298

(51) Int. Cl.
 *C07H 21/04* (2006.01)
 *C12N 15/82* (2006.01)
 *A01H 5/00* (2006.01)

(52) U.S. Cl. .................. 536/24.1; 800/320.3; 800/287; 800/298; 435/419; 435/468

(58) Field of Classification Search ........................ None
See application file for complete search history.

(56) References Cited

U.S. PATENT DOCUMENTS

2007/0016976 A1    1/2007   Katagiri et al. ............. 800/279

FOREIGN PATENT DOCUMENTS

| EP | 0913469 A1 | 5/1999 |
|---|---|---|
| WO | WO 98/22593 A1 | 5/1998 |
| WO | WO 99/09190 A1 | 2/1999 |

OTHER PUBLICATIONS

Han et al. Oryza sativa genomic DNA, chromosome X, BAC clone: H0421H08, complete sequence. (2000) GenBank Accession AL442117; pp. 1-17.*
van Knippenberg et al. (2004), In vitro transcription of *Tomato spotted wilt virus* is independent of translation, *J. Gen. Virol.* 85:1335-1338.
Kay et al. (1987), Duplication of CaMV 35S promoter sequences creates a strong enhancer for plant genes, *Science.* 236:1299-1302.
Cocciolone et al. (2000), Hierachical patterns of transgene expression indicate involvement of developmental mechanisms in the regulation of the maize *P1-rr* promoter, *Genetics.* 156:839-846.
Database EM_HTG, EBI Hinxton, GB AC/ID No. AP004068, Sasaki T et al.: "Oryza sativa nipponbare (GA3) genomic DNA, chromosome 2, BAC", XP002188680 (Aug. 17, 2001).

* cited by examiner

*Primary Examiner*—Cathy Kingdon Worley
(74) *Attorney, Agent, or Firm*—Howrey LLP

(57) ABSTRACT

The abundance of the 96 most abundant EST cluster sequences in a wheat lemma/palea cDNA library was investigated in a range of cDNA libraries made from various wheat tissues. 30 cDNA sequences showing highly enhanced abundance in lemma, palea and glume tissues over leaf, stem, embryo, endosperm and root tissue were selected for further analysis. These wheat EST cluster sequences were used to identify rice cDNA homologs. The abundance of the rice cDNA homologs was compared in rice leaf and panicle (includes lemma and palea) cDNA libraries. Rice cDNAs showing preferential expression in the panicle were then used to identify homologous rice genomic DNA clones, the putative promoter sequences have been identified and cloned.

18 Claims, 6 Drawing Sheets

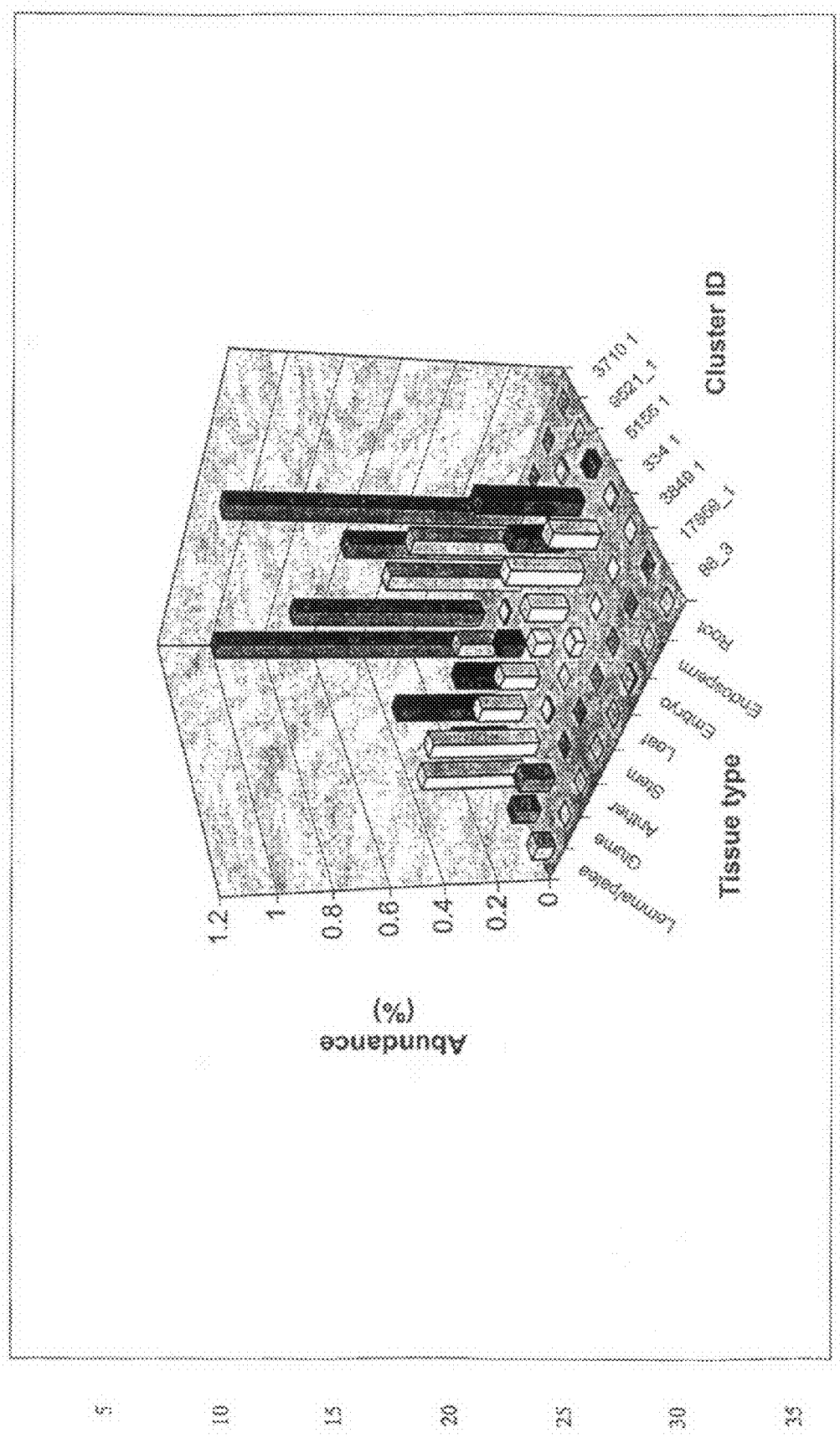
Figure 1. Wheat EST cluster % abundance in a range of cDNA libraries measured by BLAST

```
gDNA  CTAGTGAAAAAGATAACTGTGCAAGCTAGCTTCTCGCTCTCGCGCCTATAAATTGGGCGCTCGCCGCCGGCCTCAGAGTG   80 prot.                                                                           M  A
cDNA            ACACAGACGCACTCACACACTCAGCTTAAGCGAGCGAGCGAGTGAACGAGAGAGAGACAGAGATGGC
gDNA  CACACACAGACACAGACGCACTCACACACTCAGCTTAAGCGAGCGAGCGAGTGAACGAGAGAGAGAGAGACAGAGATGGC  160 prot.   S  V  A  S  F  P  V  I  N  M  E  N  L  E  T  E  E  R  G  A  A  M  E  V  I  R  D
cDNA  GAGTGTTGCCTCCTTCCCGGTGATCAACATGGAGAACCTGGAGACCGAGGAGAGGGGCCGCAGCAATGGAGGTCATCCGCG
gDNA  GAGTGTTGCCTCCTTCCCGGTGATCAACATGGAGAACCTGGAGACCGAGGAGAGGGGCCGCAGCAATGGAGGTCATCCGCG  240 prot.   A  C  E  N  W  G  F  F  E
cDNA  ACGCCTGCGAGAACTGGGGCTTCTTCGAG-------------------------------------------------
gDNA  ACGCCTGCGAGAACTGGGGCTTCTTCGAGGTGCATATGCATGCCAAGCACTAGCATGTACTAACCAGCAAAAATGTTA   320
```

Figure 2. LP1 promoter identification. Alignment of rice genomic DNA fragment (gDNA - OSM13175) and 5' terminus of rice cDNA cluster (cDNA - 109_1.R2011) with putative translation product in single letter amino acid code (prot.). Putative TATA box in bold and underlined, ATG translation start codon in bold and intron indicated by hyphens in cDNA sequence.

```
gDNA  CTTGTCAGGTGCCAACAAACAGCATCTTGGCGTACATAAGCTATATAGAGGATTAAAAGGAATGTTTTGTTCCTTGCTA    80 gDNA  CTGTTTTTTAACCTGTTTACTCAGGAGACAAATTTGTTGCATAAACCATTTGTTCTAGGGATCAGTATTGTCCTCTCAGT   160 gDNA  GTGTTATGTAAGCATTTCCAGAAATCAATTGTCGCTATCAGCTTCCCTCACATTAGCTATCACTTATACCCCTTTTTTTC   240 gDNA  TCATAGGCTCACCATGTCCATTTTATTCATGATATTTCTTTGTCTAAAGTATGTGAAATACCATTTTATGCAGATAGGAG   320 prot.           M   A   A   L   D   T   F   L   F   T   S   E   S   V   N   E   G   H   P   D   K   L   C   D   Q   V
gDNA  AAGATGGCCGCACTTGATACCTTCCTCTTTACCTCGGAGTCTGTGAACGAGGGCCACCCTGACAAGCTCTGCGACCAAGT   400 prot.   S   D   A   V   L   D   A   C   L   A   E   D   P   D   S   K   V   A   C   E   T   C   T   K   T   N   M
cDNA          CAGATGCTGTGCTTGATGCTTGCCTCGCCGAGGACCCTGACAGCAAGGTCGCTTGTGAGACCTGCACCAAGACAAACA
gDNA  CTCAGATGCTGTGCTTGATGCTTGCCTCGCCGAGGACCCTGACAGCAAGGTCGCTTGTGAGACCTGCACCAAGACAAACA   480 prot.   V   M   V   F   G   E   I   T   T   K   A   N   V   D   Y   E   K   I   V   R   E   T   C   R   N   I
cDNA  TGGTCATGGTCTTTGGTGAGATCACCACCAAGGCTAACGTTGACTATGAGAAGATTGTCAGGGAGACATGCCGTAACATC
gDNA  TGGTCATGGTCTTTGGTGAGATCACCACCAAGGCTAACGTTGACTATGAGAAGATTGTCAGGGAGACATGCCGTAACATC   560
```

Figure 3. LP3 promoter identification. Alignment of rice genomic DNA fragment (gDNA) and 5' terminus of rice cDNA cluster (cDNA - 618_3.R2011) with putative translation product in single letter amino acid code (prot.). Putative TATA box in bold and underlined and ATG translation start codon in bold.

```
gDNA   GAGGTGGGGCCCAGTGCGGGTATGAAGCGGGGAGGCGCTATATAGAGCCGCACCCATCCTCCTCCCCCTTCCTCCCTCTCC    80 cDNA   TCTCCACTACTAATACCACCACCGCCGCCGCCGCCCGGAGGTGGAAGACGGAGGGTAGAGTTGGGGTCTCGCGGTGAGCCGAT
gDNA   TCTCCACTACTAATACCACCACCGCCGCCGCCGCCCGGAGGTGGAAGACGGAGGGTAGAGTTGGGGTCTCGCGGTGAGCCGAT   160 prot.                                                                   M  G  G  L  E  E  I  K
cDNA   TCCTCTCTAGTGGTCGCGCCTGGTGTGTTCGCCGACGACGCCGGCTCGCGTCAGCCATGGGGTGGGCTCGAGGAGATCAA
gDNA   TCCTCTCTAGTGGTCGCGCCTGGTGTGTTCGCCGACGACGCCGGCTCGCGTCAGCCATGGGGTGGGCTCGAGGAGATCAA    240 prot.  N  E  A  V  D  L
cDNA   GAATGAGGCCGTTGATCTGG------------------------------------------------------------
gDNA   GAATGAGGCCGTTGATCTGGTGAGAAAATCACTCGCCGCCACCAGCTACCTACTTCTTCTTCCTCGCTTCCTCCCTC     320
```

Figure 4. LP4 promoter identification. Alignment of rice genomic DNA fragment (gDNA - OSM12402) and 5' terminus of rice cDNA cluster (cDNA - 5842_1.R2011) with putative translation product in single letter amino acid code (prot.). Putative TATA box in bold and underlined, ATG translation start codon in bold and intron indicated by hyphens in cDNA sequence.

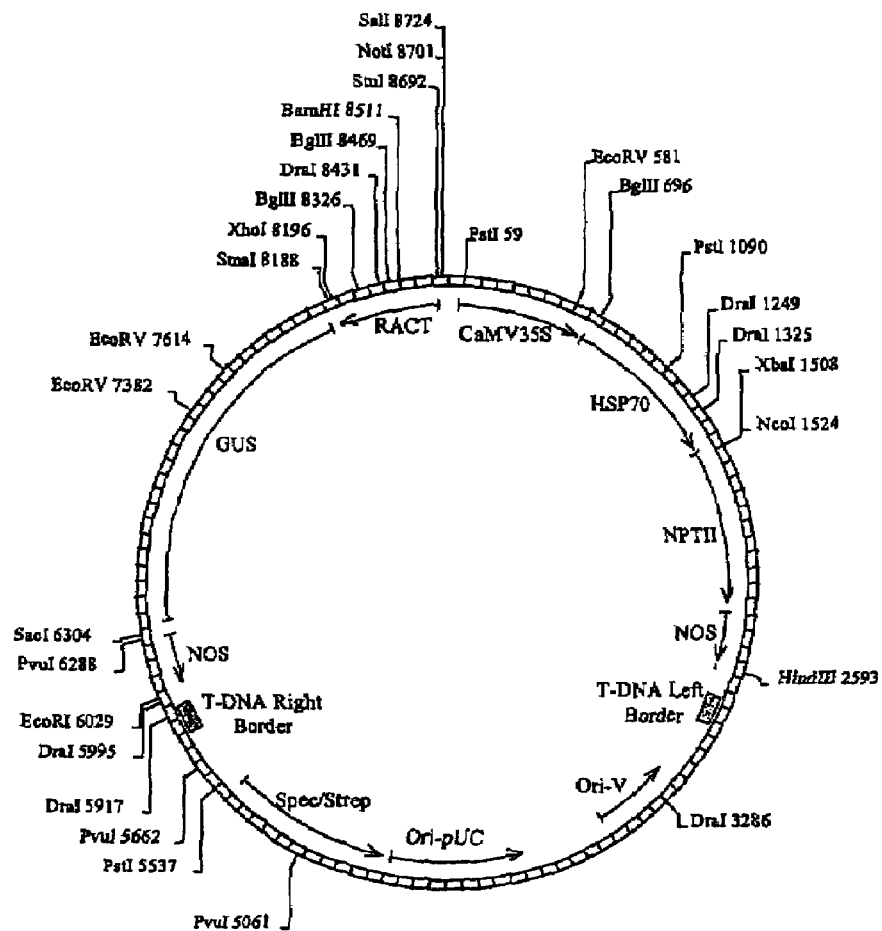
Figure 5. pMONCAM-1 binary vector used for *Agrobacterium* mediated transformation, *Sal*I (8724) and *Not*I (8701) sites were used for insertion of promoters.

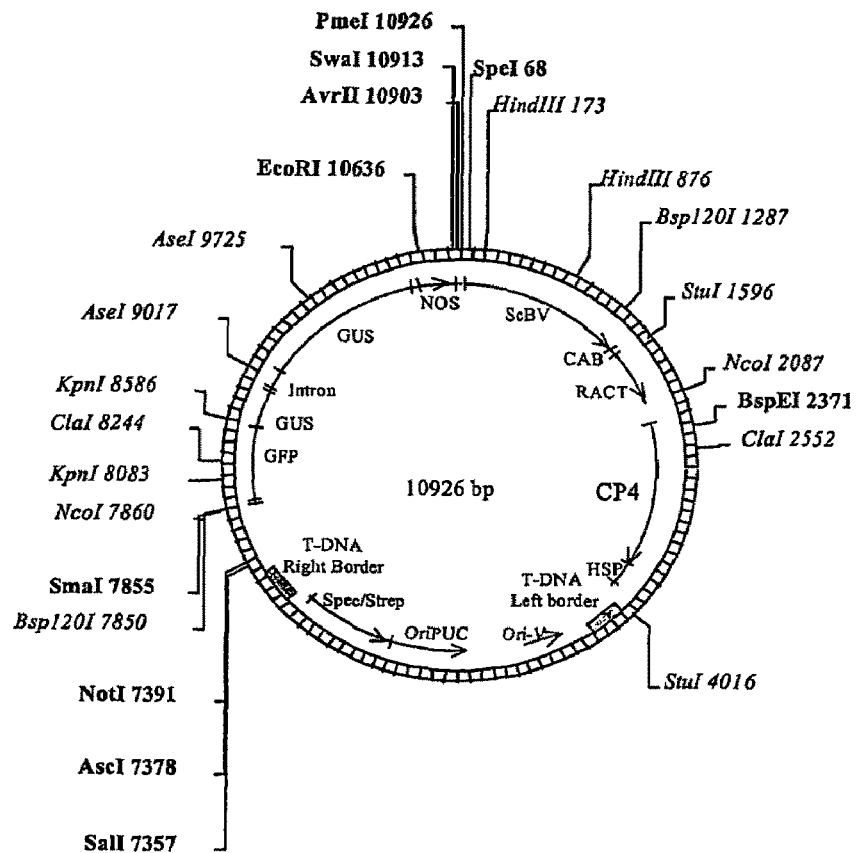
Figure 6. pMON-CAM2 binary vector used for *Agrobacterium* mediated transformation, *SalI* (7357) and *SmaI* (7855) sites were used for insertion of LP4 promoter.

RICE REGULATORY SEQUENCES FOR GENE EXPRESSION IN DEFINED WHEAT TISSUE

This application is a divisional filing of Ser. No. 10/488,149, filed Oct. 21, 2004 (now U.S. Pat. No. 7,375,208), which is a §371 national stage filing of PCT/EP02/09533, filed 23 Aug. 2002 (published in English on 13 Mar. 2003 as WO 03/020937) and claiming priority to EP 01307298.8 filed 28 Aug. 2001.

FIELD OF THE INVENTION

The present invention relates to isolated nucleic acid molecules, specifically regulatory sequences, more specifically rice promoters and the use thereof for controlling gene expression in predefined wheat tissue such as glume, lemma and/or palea. A method of isolating those regulatory sequences is also disclosed.

BACKGROUND OF THE INVENTION

*Fusarium* head blight of small grains ("scab"), often referred to by the acronym "FHB", is increasing world wide and is a tremendous problem for the production and yield of wheat. Within the last dozen years there have been outbreaks of FHB in the midwestern and eastern states in the USA, as well as in central and eastern Canada. The most extended recent episode has been in the spring grain region of the upper midwest, centered on the Red River Valley of North Dakota, Minn., and Manitoba. Here, there have been five consecutive years of severe disease. Losses have been large, and accumulated loss has brought ruin to many farmers.

While several species of the soil- and residue-borne fungus *Fusarium* are capable of inciting FHB, most of the damage in recent outbreaks in the US and Canada has been due to *F. graminearum*. In addition to grain crops, this species has a wide host range among grasses. The name *Fusarium*, in fact, means "of the grasses". This species was probably present in native grassland long before wheat or barley arrived in North America. *F. graminearum* is also a superb colonizer of senescent plants; especially corn stalks. *F. graminearum* is unique in another regard. It is the only common *Fusarium* species infecting wheat which regularly and abundantly forms its sexual stage (*Gibberella zeae*) in nature. Because the spores produced by this stage are forcibly shot into the air, they greatly increase the ability of the fungus to disperse from colonized crop residue where the fruit-bodies (perithecia) of this stage form.

*F. graminearum* has a complex life cycle which is easier to picture if it is divided in two parts: a pathogenic cycle, and a 'hidden' cycle of saprophytic colonization. The effect of the pathogenic cycle is seen as FHB. Aerial spores land on flowering heads during wet weather and FHB results. *F. graminearum* survives on the residue; particularly on infected heads, and sporulates the next spring and summer. In the saprophytic cycle mycelium superficially occupy cornstalks, often without causing disease. At senescence, invasive colonization occurs and *F. graminearum* takes possession of most of the corn stalk residue. One Minnesota study found over 80% of the corn stalk residue in fall was occupied by *F. graminearum* and it covers over 60% the following spring. This colonized residue provides a site for massive sporulation during the next growing season. Those airborne spores may begin new saprophytic colonization or they may initiate pathogenic cycles resulting in FHB. The saprophytic colonization cycle is the engine that drives the pathogenic part of the cycle.

The saprophytic life cycle of *F. graminearum* is fueled by corn stalk residue. There are a number of observations that when corn production moves into a previously small grain area, the occurrence of *F. graminearum* and the risk of FHB increase. Combine the extension of corn acreage into wheat and barley country with large increases in reduced tillage and the stage is set for major epidemics of FHB in small grains when the weather favoring disease occurs.

Thus *Fusarium* head blight disease can affect a number of cereal crops such as wheat, barley, rice, rye and maize. It is caused by the phytopathogenic fungi *Fusarium graminearum, F. moniliforme, F. culmorum, F. nivale* and *Microdochium nivale*. Moist environmental conditions during anthesis can result in *Fusarium* epidemics and huge losses in crop revenues. The disease not only reduces crop yield and grain quality but also leads to fungal mycotoxin accumulation in grain.

Kang et al., (Mycol. Res. 104(9): 1083-1093, 2000) disclose experimental evidence that penetration of host tissues by *Fusarium culmorum* occurred on the inner surfaces of lemma, glume and palea as early as 36 h after inoculation demonstrating that glume, lemma and/or palea are the key entry points for start of the infection process by *Fusarium* in wheat.

One of the goals of plant genetic engineering is to produce plants with agronomically important characteristics or traits. Recent advances in genetic engineering have provided the requisite tools to transform plants to contain and express foreign genes (Kahl et al., 1995, World Journal of Microbiology and Biotechnology 11:449-460). Particularly desirable traits or qualities of interest for plant genetic engineering would include, but are not limited to, resistance to insects, fungal diseases such as the *Fusarium* head blight disease, and other pests and disease-causing agents, tolerances to herbicides, enhanced yield stability or shelf-life, environmental tolerances, and nutritional enhancements. The technological advances in plant transformation and regeneration have enabled researchers to take pieces of DNA, such as a gene or genes from a heterologous source, or a native source, but modified to have different or improved qualities, and incorporate the exogenous DNA into the plant's genome. The gene or gene(s) can then be expressed in the plant cell to exhibit the added characteristic(s) or trait(s). In one approach, expression of a novel gene that is not normally expressed in a particular plant or plant tissue may confer a desired phenotypic effect. In another approach, transcription of a gene or part of a gene in an antisense orientation may produce a desirable effect by preventing or inhibiting expression of an endogenous gene.

Isolated plant promoters are useful for modifying plants through genetic engineering to have desired phenotypic characteristics. In order to produce such a transgenic plant, a vector that includes a heterologous gene sequence that confers the desired phenotype when expressed in the plant is introduced into the plant cell. The vector also includes a plant promoter that is operably linked to the heterologous gene sequence, often a promoter not normally associated with the heterologous gene. The vector is then introduced into a plant cell to produce a transformed plant cell, and the transformed plant cell is regenerated into a transgenic plant. The promoter controls expression of the introduced DNA sequence to which the promoter is operably linked and thus affects the desired characteristic conferred by the DNA sequence.

Because the promoter is a regulatory element that plays an integral part in the overall expression of a gene or genes, it would be advantageous to have a variety of promoters to tailor gene expression such that a gene or genes is transcribed efficiently at the right time during plant growth and development, in the optimal location in the plant, and in the amount necessary to produce the desired effect. In one case, for example, constitutive expression of a gene product may be beneficial in one location of the plant, but less beneficial in another part of the plant. In other cases, it may be beneficial to have a gene product produced at a certain developmental stage of the plant, or in response to certain environmental or chemical stimuli. The commercial development of genetically improved germplasm has also advanced to the stage of introducing multiple traits into crop plants, often referred to as a gene stacking approach. In this approach, multiple genes conferring different characteristics of interest can be introduced into a plant. It is important when introducing multiple genes into a plant, that each gene is modulated or controlled for optimal expression and that the regulatory elements are diverse, to reduce the potential of gene silencing that can be caused by recombination of homologous sequences. In light of these and other considerations, it is apparent that optimal control of gene expression and regulatory element diversity are important in plant biotechnology.

The proper regulatory sequences must be present in the proper location with respect to the DNA sequence of interest for the newly inserted DNA to be transcribed and thereby, if desired, translated into a protein in the plant cell. These regulatory sequences include, but are not limited to, a promoter, a 5' untranslated leader, and a 3' polyadenylation sequence. The ability to select the tissues in which to transcribe such foreign DNA and the time during plant growth in which to obtain transcription of such foreign DNA is also possible through the choice of appropriate promoter sequences that control transcription of these genes.

A variety of different types or classes of promoters can be used for plant genetic engineering. Promoters can be classified on the basis of range of tissue specificity. For example, promoters referred to as constitutive promoters are capable of transcribing operatively linked DNA sequences efficiently and expressing said DNA sequences in multiple tissues. Tissue-enhanced or tissue-specific promoters can be found upstream and operatively linked to DNA sequences normally transcribed in higher levels in certain plant tissues or specifically in certain plant tissues. Other classes of promoters would include, but are not limited to, inducible promoters that can be triggered by external stimuli such as chemical agents, developmental stimuli, or environmental stimuli. Thus, the different types of promoters desired can be obtained by isolating the regulatory regions of DNA sequences that are transcribed and expressed in a constitutive, tissue-enhanced, or inducible manner.

The technological advances of high-throughput sequencing and bioinformatics has provided additional molecular tools for promoter discovery. Particular target plant cells, tissues, or organs at a specific stage of development, or under particular chemical, environmental, or physiological conditions can be used as source material to isolate the mRNA and construct cDNA libraries. The cDNA libraries are quickly sequenced, and the expressed sequences can be catalogued electronically. Using sequence analysis software, thousands of sequences can be analyzed in a short period, and sequences from selected cDNA libraries can be compared. The combination of laboratory and computer-based subtraction methods allows researchers to scan and compare cDNA libraries and identify sequences with a desired expression profile. For example, sequences expressed preferentially in one tissue can be identified by comparing a cDNA library from one tissue to cDNA libraries of other tissues and electronically "subtracting" common sequences to find sequences only expressed in the target tissue of interest. The tissue enhanced sequence can then be used as a probe or primer to clone the corresponding full-length cDNA. A genomic library of the target plant can then be used to isolate the corresponding gene and the associated regulatory elements, including but not limited to promoter sequences.

Despite all the technology currently available no monocotyledonous regulatory sequences capable of regulating transcription of an operably linked nucleic acid sequence in lemma, palea and/or glume monocotyledonous tissue are known. More specifically wheat promoters which could drive expression of a gene in the palea, glume and/or lemma of wheat are unfortunately also unknown. Since the palea, glume and/or lemma are the key entry points susceptible to *Fusarium* attack, it is highly desirable to have access to specific promoters which can, for instance, drive expression of a heterologous gene able to prevent and/or cure *Fusarium* attack and/or related disease in these specific tissues.

SUMMARY OF THE INVENTION

The current invention discloses a solution to the above problems in the provision of newly isolated monocotyledonous regulatory sequences capable of regulating transcription of an operably linked nucleic acid sequence in lemma, palea and/or glume monocotyledonous tissue. In order to isolate these new monocotyledonous regulatory sequences the following inventive non-obvious process has been developed. Firstly, tissue specific EST's have been found; secondly specific homologues in another species e.g. rice have been located. Subsequently for these specific homologues e.g. in rice, it has been determined that they are expressed in the appropriate tissue specific manner. Using the genomic DNA sequence the promoters have been cloned from the other species i.e. rice or maize.

More in detail the abundance of the 96 most abundant EST cluster sequences in a wheat lemma/palea cDNA library was investigated in a range of cDNA libraries made from various wheat and maize tissues. 30 cDNA sequences showing highly enhanced abundance in lemma, palea and glume tissues over leaf, stem, embryo, endosperm and root tissue were selected for further analysis. These wheat EST cluster sequences were used to identify e.g. rice cDNA homologs. The abundance of the rice cDNA homologs was compared in rice leaf and panicle (includes lemma and palea) cDNA libraries. Rice cDNAs showing preferential expression in the panicle were then used to identify homologous rice genomic DNA clones; the putative promoter sequences have been identified and cloned.

The isolation of heterologous promoters via a homolog intermediate cDNA has two main advantages. Firstly identification of promoters with a conserved gene expression pattern across species and, secondly, confident identification of the correct gene family member for subsequent promoter isolation.

BRIEF DESCRIPTION OF THE DRAWINGS

FIG. 1: Shown is the wheat EST cluster % abundance in a range of cDNA libraries as measured by BLAST.

FIG. 2: LP1 promoter identification. Shown is an alignment of a rice genomic DNA (gDNA) fragment (SEQ ID NO:4) and 5' terminal cDNA sequence (SEQ ID NO:5) with a putative translation product (prot., SEQ ID NO:6). A putative TATA box is shown in bold and underlined. The ATG translation start codon is shown in bold and an intron is indicated by hyphens in the cDNA sequence line.

FIG. 3: LP3 promoter identification. Shown is an alignment of a rice gDNA fragment (SEQ ID NO:7) and 5' terminal cDNA sequence (SEQ ID NO:8) with a putative translation product (prot., SEQ ID NO:9). A putative TATA box is shown in bold and underlined. The ATG translation start codon is shown in bold.

FIG. 4: LP4 promoter identification. Shown is an alignment of a rice gDNA fragment (SEQ ID NO:10) and 5' terminal cDNA sequence (SEQ ID NO:11) with a putative translation product (prot., SEQ ID NO:12). A putative TATA box is shown in bold and underlined. The ATG translation start codon is shown in bold and an intron is indicated by hyphens in the cDNA sequence line.

FIG. 5: Shown is the pMON-CAM-1 binary vector used for *Agrobacterium*-mediated transformation. SalI (8724) and NotI (8701) restriction sites were used for insertion of certain promoters.

FIG. 6: Shown is the pMON-CAM-2 binary vector used for *Agrobacterium*-mediated transformation. SalI (7357) and SmaI (7855) restriction sites were used for insertion of the LP4 promoter.

DETAILED DESCRIPTION OF THE INVENTION

The present invention thus provides isolated plant promoter sequences, preferably monocotyledonous regulatory sequences that comprise nucleic acid regions located upstream of the 5' end of structural coding sequences that are transcribed in defined monocot, more specifically in wheat tissues such as lemma, palea and/or glume. Said promoter sequences are capable of modulating or initiating transcription of DNA sequences to which they are operably linked in specific, well-defined monocotyledonous tissue. In addition to regulatory elements or sequences located upstream (5') or within a DNA sequence, there are downstream (3') sequences that affect gene expression and thus the term "regulatory sequence" as used herein refers to any nucleotide sequence located upstream, within, or downstream to a DNA sequence that controls, mediates, or affects expression of a gene product in conjunction with the protein synthetic apparatus of the cell.

The present invention provides nucleic acid sequences comprising monocotyledonous regulatory sequences exemplified in SEQ ID NOS: 1-3 that are located upstream of the 5' end of structural coding sequences and transcribed in monocotyledonous tissue, more specifically in wheat tissue preferably lemma, palea or glume.

In one aspect, the present invention provides nucleic acid sequences comprising a sequence selected from the group consisting of SEQ ID NOS: 1-3 or any fragments or regions of the sequence or cis elements of the sequence that are capable of regulating transcription of operably linked DNA sequences.

The present invention also provides nucleic acid sequences comprising a sequence selected from the group consisting of SEQ ID NOS: 1-3 that are promoters.

Another aspect of the present invention relates to the use of one or more cis elements, or fragments thereof of the disclosed 5' promoter sequences that can be combined to create novel promoters or used in a novel combination with another heterologous regulatory sequence to create a chimeric or hybrid promoter capable of modulating transcription of an operably linked DNA sequence.

Hence, the present invention relates to the use of nucleic acid sequences disclosed in SEQ ID NOS: 1-3 or any fragment, region, or cis element of the disclosed sequences that are capable of regulating transcription of a DNA sequence when operably linked to the DNA sequence. Therefore, the invention not only encompasses the sequences as disclosed in SEQ ID NOS: 1-3, but also includes any truncated or deletion derivatives, or fragments or regions thereof that are capable of functioning independently as a promoter including cis elements that are capable of functioning as regulatory sequences in conjuction with one or more regulatory sequences when operably linked to a transcribable sequence.

The present invention thus encompasses a novel promoter or chimeric or hybrid promoter comprising a nucleic acid of SEQ ID NOS: 1-3. The chimeric or hybrid promoters can consist of any length fragments, regions, or cis elements of the disclosed sequences of SEQ ID NOS: 1-3 combined with any other transcriptionally active minimal or full-length promoter. For example, a promoter sequence selected from SEQ ID NOS: 1-3 may be combined with a CaMV 35S or other promoter, such as a rice actin promoter, to construct a novel chimeric or hybrid promoter. A minimal promoter can also be used in combination with the nucleic acid sequences of the present invention. A novel promoter also comprises any promoter constructed by engineering the nucleic acid sequences disclosed in SEQ ID NOS: 1-3 or any fragment, region, or cis element of the disclosed sequences in any manner sufficient to transcribe an operably linked DNA sequence.

Another aspect of the present invention relates to the ability of the promoter sequences of SEQ ID NOS: 1-3 or fragments, regions, or cis elements thereof to regulate transcription of operably linked transcribable sequences in specific floral tissues. Fragments, regions, or cis elements of SEQ ID NOS: 1-3 that are capable of regulating transcription of operably linked DNA sequences in certain tissues may be isolated from the disclosed nucleic acid sequences of SEQ ID NOS: 1-3 and used to engineer novel promoters.

The present invention also encompasses DNA constructs comprising the disclosed sequences as shown in SEQ ID NOS: 1-3 or any fragments, regions, or cis elements thereof, including novel promoters generated using the disclosed sequences or any fragment, region, or cis element thereof.

The present invention also includes any transgenic plant cell and plants containing the DNA disclosed in the sequences as shown in SEQ ID NOS: 1-3 or any fragments, regions, or cis elements thereof.

The present invention also provides a method of regulating transcription of a DNA sequence comprising operably linking the DNA sequence to any promoter comprising a nucleic acid sequence comprising all or any fragment, region or cis element of a sequence selected from the group consisting of SEQ ID NOS: 1-3 wherein said promoter confers enhanced or decreased expression of the operably linked DNA sequence.

In another embodiment the present invention provides a method of regulating expression of DNA sequences in monocotyledonous tissues preferably lemma, palea or glume of wheat by operably linking a sequence selected from the group consisting of SEQ ID NOS: 1-3 or any fragment, region, or cis element of the disclosed sequences to any transcribable DNA sequence. The fragments, regions, or cis elements of the disclosed promoters as shown in SEQ ID NOS: 1-3 can be engineered and used independently in novel combinations including multimers, or truncated derivatives and the novel promoters can be operably linked with a transcribable DNA sequence. Alternatively the disclosed fragments, regions, or cis elements of the disclosed sequences can be used in combination with a heterologous promoter including a minimal promoter to create a novel chimeric or hybrid promoter and the novel chimeric promoter can be operably linked to a transcribable DNA sequence.

The present invention also provides a method of producing a transgenic plant by introducing into a plant cell a DNA construct comprising: (i) a promoter comprising a nucleic acid comprising a sequence selected from the group consisting of SEQ ID NOS: 1-3 or fragment, region, or cis element thereof, and operably linked to the promoter, (ii) a transcribable DNA sequence and (iii) a 3' untranslated region. For transformation purposes in addition an appropriate selectable marker cassette may be used in order to establish and recognize transformed plants. Useful markers are hereafter exemplified in this application.

The present invention also encompasses differentiated plants, seeds and progeny comprising above mentioned transformed plant cells. The plants thus obtained show tissue specific expression of so-called reporter genes. Said promoters can thus be used in a proper construct to enable expression of control genes against for instance *Fusarium* head blight disease in the right tissue. Such transformed plants thus obtained exhibit novel properties of agronomic significance.

The present invention also provides a method of isolating 5' regulatory sequences of a desired expression profile from a target plant of interest by evaluating a collection of nucleic acid sequences of ESTs derived from one or more cDNA libraries prepared from a plant cell type of interest, comparing EST sequences from at least one target plant cDNA library and one or more non-target cDNA libraries of ESTs from a different plant cell type, subtracting common EST sequences found in both target and non-target libraries, designing gene-specific primers from the remaining ESTs after the subtraction that are representative of the targeted expressed sequences, and isolating the corresponding 5' flanking and regulatory sequences, that includes promoter sequences from a genomic DNA database prepared from the target plant using the gene specific primers.

The foregoing and other aspects of the invention will become more apparent from the following detailed description of definitions and methods used and accompanying drawings as well.

DEFINITIONS AND METHODS

The following definitions and methods are provided to better define the present invention and to guide those of ordinary skill in the art in the practice of the present invention. Unless otherwise noted, terms are to be understood according to conventional usage by those of ordinary skill in the relevant art. The standard one- and three-letter nomenclature for amino acid residues is used.

"Nucleic acid (sequence)" or "polynucleotide (sequence)" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence that originates from a foreign source or species or, if from the same source, is modified from its original form.

An "isolated" nucleic acid sequence is substantially separated or purified away from other nucleic acid sequences that the nucleic, acid is normally associated with in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

The term "substantially purified", as used herein, refers to a molecule separated from substantially all other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

A first nucleic acid sequence displays "substantial identity" to a reference nucleic acid sequence if, when optimally aligned (with appropriate nucleotide insertions or deletions totaling less than 20 percent of the reference sequence over the window of comparison) with the other nucleic acid (or its complementary strand), there is at least about 75% nucleotide sequence identity, preferably at least about 80% identity, more preferably at least about 85% identity, and most preferably at least about 90% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman (Adv. Appl. Math. 2: 482, 1981); by the homology alignment algorithm of Needleman and Wunsch (J. Mol. Biol. 48:443, 1970); by the search for similarity method of Pearson and Lipman (Proc. Natl. Acad. Sci. USA 85:2444, 1988); preferably by computerized implementations of these algorithms (GAP, BESTFIT, FASTA, and TFASTA) in the Wisconsin Genetics Software Package Release 7.0 (Genetics Computer Group, 575 Science Dr., Madison, Wis.). The reference nucleic acid may be a full-length molecule or a portion of a longer molecule. Alternatively, two nucleic acids have substantial identity if one hybridizes to the other under stringent conditions, as defined below.

A first nucleic acid sequence is "operably linked" with a second nucleic acid sequence when the sequences are so arranged that the first nucleic acid sequence affects the function of the second nucleic acid sequence. Preferably, the two sequences are part of a single contiguous nucleic acid molecule and more preferably are adjacent. For example, a promoter is operably linked to a gene if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., Molecular Cloning: A Laboratory Manual, 2nd ed., vol. 1-3, ed. Sambrook et al., Cold Spring Harbor Laboratory Press, Cold Spring Harbor, N.Y., 1989, Sambrook et al., 1989; Current Protocols in Molecular Biology, ed. Ausubel et al., Greene Publishing and Wiley-Interscience, New York, 1992, with periodic updates, Ausubel et al., 1992; and PCR Protocols: A Guide to Methods and Applications, Academic Press: San Diego, Innis et al., 1990). Methods for chemical synthesis of nucleic acids are discussed, for example, in Beaucage and Carruthers (Tetra. Letts. 22:1859-1862, 1981), and Matteucci et al. (J. Am. Chem. Soc. 103:3185, 1981). Chemical synthesis of nucleic acids can be performed, for example, on commercial automated oligonucleotide synthesizers.

A "synthetic nucleic acid sequence" can be designed and chemically synthesized for enhanced expression in particular host cells and for the purposes of cloning into appropriate vectors. Synthetic DNAs designed to enhance expression in a particular host should therefore reflect the pattern of codon usage in the host cell. Computer programs are available for these purposes including but not limited to the "BestFit" or "Gap" programs of the Sequence Analysis Software Package, Genetics Computer Group, Inc. (University of Wisconsin Biotechnology Center, Madison, Wis. 53711).

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and by Innis et al. (PCR Protocols: A Guide to Methods and Applications, Academic Press, San Diego, 1990). In PCR, a primer refers to a short oligonucleotide of defined sequence that is annealed to a DNA template to initiate the polymerase chain reaction.

"Transformed", "transfected", or "transgenic" refers to a cell, tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g., rRNA, tRNA); and other types of genes function as regulators of expression (regulator genes).

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element that may also be a component or part of an expression vector. Examples of genetic components include, but are not limited to, promoter regions, 5' untranslated leaders, introns, genes, 3' untranslated regions, and other regulatory sequences or sequences that affect transcription or translation of one or more nucleic acid sequences.

The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

"Complementary" refers to the natural association of nucleic acid sequences by base-pairing (A-G-T pairs with the complementary sequence A-C-T). Complementarity between two single-stranded molecules may be partial, if only some of the nucleic acids pair are complementary, or complete, if all bases pair are complementary. The degree of complementarity affects the efficiency and strength of hybridization and amplification reactions.

"Homology" refers to the level of similarity between nucleic acid or amino acid sequences in terms of percent nucleotide, or amino acid positional identity, respectively, i.e., sequence similarity or identity. Homology also refers to the concept of similar functional properties among different nucleic acids or proteins.

"ESTs" or Expressed Sequence Tags are short sequences of randomly selected clones from a cDNA (or complementary DNA) library that are representative of the cDNA inserts of these randomly selected clones (McCombie et al., Nature Genetics, 1:124, 1992; Kurata et al., Nature Genetics, 8: 365,1994; Okubo et al., Nature Genetics, 2: 173, 1992).

The term "electronic Northern" refers to a computer-based sequence analysis that allows sequences from multiple cDNA libraries to be compared electronically based on parameters the researcher identifies including abundance in EST populations in multiple cDNA libraries, or exclusively to EST sets from one or combinations of libraries.

"Subsetting" refers to a method of comparing nucleic acid sequences from different or multiple sources that can be used to assess the expression profile of the nucleic acid sequences that reflects gene transcription activity and message stability in a particular tissue, at a particular time, or under particular conditions.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example, by chemical compounds (chemical inducers) or in response to environmental, hormonal, chemical, or, developmental signals. Inducible or regulated promoters include, for example, promoters regulated by light, heat, stress, flooding or drought, phytohormones, wounding, or chemicals such as ethanol, jasmonate, salicylic acid, safeners, pests or pathogens.

Any plant promoter can be used as a 5' regulatory sequence for modulating expression of a particular gene or genes. One preferred promoter would be a plant promoter that recognizes and binds RNA polymerase II. Such plant RNA polymerase type II promoters, like those of other higher eukaryotes, have complex structures and are comprised of several distinct elements. One such element is the TATA box or Goldberg-Hogness box, which is required for correct expression of eukaryotic genes in vitro and accurate, efficient initiation of transcription in vivo. The TATA box is typically positioned at approximately −25 to −35, that is, at 25 to 35 basepairs (bp)

upstream (5') of the transcription initiation site, or cap site, which is defined as position +1 (Breathnach and Chambon, Ann. Rev. Biochem. 50:349-383, 1981; Messing et al., In: Genetic Engineering of Plants, Kosuge et al., eds., pp. 211-227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: Genetic Engineering of Plants, Kosuge et al., eds., pp. 211-227, 1983). In addition, virtually all promoters include additional upstream activating sequences or enhancers (Benoist and Chambon, Nature 290: 304-310, 1981; Gruss et al., Proc. Natl. Acad. Sci. USA 78:943-947, 1981; and Khoury and Gruss, Cell 27:313-314, 1983) extending from around −100 bp to −1,000 bp or more upstream of the transcription initiation site. Enhancers have also been found 3' to the transcriptional start site.

When fused to heterologous DNA sequences, such promoters typically cause the fused sequence to be transcribed in a manner that is similar to that of the gene sequence that the promoter is normally associated with. Promoter fragments that include regulatory sequences can be added (for example, fused to the 5' end of, or inserted within, an active promoter having its own partial or complete regulatory sequences (Fluhr et al., Science 232:1106-1112, 1986; Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant Mol. Biol. 15:373-381, 1991). Alternatively, heterologous regulatory sequences can be added to the 5' upstream region of an inactive, truncated promoter, e.g., a promoter including only the core TATA and, sometimes, the CCAAT elements (Fluhr et al., Science 232:1106-1112, 1986; Strittmatter and Chua, Proc. Nat. Acad. Sci. USA 84:8986-8990, 1987; Aryan et al., Mol. Gen. Genet. 225:65-71, 1991).

Promoters are typically comprised of multiple distinct "cis-acting transcriptional regulatory elements," or simply "cis-elements," each of which appears to confer a different aspect of the overall control of gene expression (Strittmatter and Chua, Proc. Nat. Acad. Sci. USA 84:8986-8990, 1987; Ellis et al., EMBO J. 6:11-16, 1987; Benfey et al., EMBO J. 9:1677-1684, 1990). Cis elements bind trans-acting protein factors that regulate transcription. Some cis elements bind more than one factor, and trans-acting transcription factors may interact with different affinities with more than one cis element (Johnson and McKnight, Ann. Rev. Biochem. 58:799-839, 1989). Plant transcription factors, corresponding cis elements, and analysis of their interaction are discussed, for example, in Martin (Curr. Opinions Biotech. 7:130-138, 1996), Murai (Methods in Plant Biochemistry and Molecular Biology, Dashek, ed., CRC Press, 1997, pp. 397-422), and Maliga et al. (Methods in Plant Molecular Biology, Cold Spring Harbor Press, 1995, pp. 233-300). The promoter sequences of the present invention can contain "cis elements" that can confer or modulate gene expression.

Cis elements can be identified by a number of techniques, including deletion analysis, i.e., deleting one or more nucleotides from the 5' end or internal to a promoter; DNA binding protein analysis using Dnase I footprinting; methylation interference; electrophoresis mobility-shift assays, in vivo genomic footprinting by ligation-mediated PCR; and other conventional assays; or by sequence similarity with known cis element motifs by conventional sequence comparison methods. The fine structure of a cis element can be further studied by mutagenesis (or substitution) of one or more nucleotides or by other conventional methods (see for example, Methods in Plant Biochemistry and Molecular Biology, Dashek, ed., CRC Press, 1997, pp. 397-422; and Methods in Plant Molecular Biology, Maliga et al., eds., Cold Spring Harbor Press, 1995, pp. 233-300).

Cis elements can be obtained by chemical synthesis or by cloning from promoters that include such elements, and they can be synthesized with additional flanking sequences that contain useful restriction enzyme sites to facilitate subsequent manipulation. In one embodiment, the promoters are comprised of multiple distinct "cis-acting transcriptional regulatory elements," or simply "cis-elements," each of which appears to confer a different aspect of the overall control of gene expression (Strittmatter and Chua, Proc. Nat. Acad. Sci. USA 84:8986-8990, 1987; Ellis et al., EMBO J. 6:11-16, 1987; Benfey et al., EMBO J. 9:1677-1684, 1990). In a preferred embodiment, sequence regions comprising "cis elements" of the nucleic acid sequences of SEQ ID NOS: 1-3 are identified using computer programs designed specifically to identify cis elements, or domains or motifs within sequences.

The present invention includes cis elements of SEQ ID NOS: 1-3 or homologues of cis elements known to affect gene regulation that show homology with the nucleic acid sequences of the present invention. A number of such elements are known in the literature, such as elements that are regulated by numerous factors such as light, heat, or stress; elements that are regulated or induced by pathogens or chemicals, and the like. Such elements may either positively or negatively regulated gene expression, depending on the conditions. Examples of cis elements would include, but are not limited to, oxygen responsive elements (Cowen et al., J. Biol. Chem. 268(36):26904, 1993), light regulatory elements (see for example, Bruce and Quaill, Plant Cell 2(11): 1081, 1990; and Bruce et al., EMBO J. 10:3015, 1991), a cis element responsive to methyl jasmonate treatment (Beaudoin and Rothstein, Plant Mol. Biol. 33:835, 1997), salicylic acid responsive elements (Strange et al., Plant J. 11:1315, 1997), heat shock response elements (Pelham et al., Trends Genet. 1:31, 1985), elements responsive to wounding and abiotic stress (Loace et al., Proc. Natl. Acad. Sci. U.S.A. 89:9230, 1992; Mhiri et al., Plant Mol. Biol. 33:257, 1997), low temperature elements (Baker et al., Plant Mol. Biol. 24:701, 1994; Jiang et al., Plant Mol. Biol. 30:679, 1996; Nordin et al., Plant Mol. Biol. 21:641, 1993; Zhou et al., J. Biol. Chem. 267:23515, 1992), and drought responsive elements, (Yamaguchi et al., Plant Cell 6:251-264, 1994; Wang et al., Plant Mol. Biol. 28:605, 1995; Bray, Trends in Plant Science 2:48, 1997).

The present invention therefore encompasses fragments or cis elements of the disclosed nucleic acid molecules, and such nucleic acid fragments can include any region of the disclosed sequences. The promoter regions or partial promoter regions of the present invention as shown in SEQ ID NOS: 1-3 can contain one or more regulatory elements including but not limited to cis elements or domains that are capable of regulating expression of operably linked DNA sequences, preferably in wheat tissues such as lemma, palea or glume.

Plant promoters can include promoters produced through the manipulation of known promoters to produce synthetic, chimeric, or hybrid promoters. Such promoters can also combine cis elements from one or more promoters, for example, by adding a heterologous regulatory sequence to an active promoter with its own partial or complete regulatory sequences (Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant. Mol. Biol. 15:373-381, 1991). Chimeric promoters have also been developed by adding a heterologous regulatory sequence to the 5' upstream region of an inactive, truncated promoter, i.e., a promoter that includes only the core TATA and, optionally, the CCAAT elements (Fluhr et al., Science 232:1106-1112, 1986; Strittmatter and Chua, Proc. Nat. Acad. Sci. USA 84:8986-8990, 1987; Aryan et al., Mol. Gen. Genet. 225:65-71, 1991).

The design, construction, and use of chimeric or hybrid promoters comprising one or more of cis elements of SEQ ID NOS: 1-3 for modulating or regulating the expression of operably linked nucleic acid sequences is also encompassed by the present invention.

The promoter sequences, fragments, regions or cis elements thereof of SEQ ID NOS: 1-3 are capable of transcribing operably linked DNA sequences in specific well-defined wheat tissues such as lemma, palea or glume and therefore can selectively regulate expression of those genes in these tissues.

The promoter sequences of the present invention are useful for regulating gene expression in wheat tissues such as lemma, palea or glume. For a number of agronomic traits, transcription of a gene or genes of interest is desirable in multiple tissues in order to confer the desired characteristic(s). The availability of suitable promoters that regulate transcription of operably linked genes in selected target tissues of interest is important because it may not be desirable to have expression of a gene in every tissue, but only in certain tissues. Consequently, it is important to have a wide variety of choices of 5' regulatory elements for any plant biotechnology strategy.

The advent of genomics, which comprises molecular and bioinformatics techniques, has resulted in rapid sequencing and analyses of a large number of DNA samples from a vast number of targets, including but not limited to plant species of agronomic importance. To identify the nucleic acid sequences of the present invention from a database or collection of cDNA sequences, the first step involves constructing cDNA libraries from specific plant tissue targets of interest. Briefly, the cDNA libraries are first constructed from these tissues that are harvested at a particular developmental stage or under particular environmental conditions. By identifying differentially expressed genes in plant tissues at different developmental stages or under different conditions, the corresponding regulatory sequences of those genes can be identified and isolated. Transcript imaging enables the identification of tissue-preferred sequences based on specific imaging of nucleic acid sequences from a cDNA library. By transcript imaging as used herein is meant an analysis that compares the abundance of expressed genes in one or more libraries. The clones contained within a cDNA library are sequenced and the sequences compared with sequences from publicly available databases. Computer-based methods allow the researcher to provide queries that compare sequences from multiple libraries. The process enables quick identification of clones of interest compared with conventional hybridization subtraction methods known to those of skill in the art.

Using conventional methodologies, cDNA libraries can be constructed from the mRNA (messenger RNA) of a given tissue or organism using poly dT primers and reverse transcriptase (Efstratiadis et al., Cell 7:279, 1976; Higuchi et al., Proc. Natl. Acad. Sci. U.S.A. 73:3146, 1976; Maniatis et al., Cell 8:163, 1976; Land et al., Nucleic Acids Res. 9:2251, 1981; Okayama et al., Mol. Cell. Biol. 2:161, 1982; Gubler et al., Gene 25:263, 1983).

Several methods can be employed to obtain full-length cDNA constructs. For example, terminal transferase can be used to add homopolymeric tails of dC residues to the free 3' hydroxyl groups (Land et al., Nucleic Acids Res. 9:2251, 1981). This tail can then be hybridized by a poly dG oligo that can act as a primer for the synthesis of full length second strand cDNA. Okayama and Berg, reported a method for obtaining full-length cDNA constructs (Mol. Cell. Biol. 2:161, 1982). This method has been simplified by using synthetic primer adapters that have both homopolymeric tails for priming the synthesis of the first and second strands and restriction sites for cloning into plasmids (Coleclough et al., Gene 34:305, 1985) and bacteriophage vectors (Krawinkel et al., Nucleic Acids Res. 14:1913, 1986; Han et al., Nucleic Acids Res. 15:6304, 1987).

These strategies can be coupled with additional strategies for isolating rare mRNA populations. For example, a typical mammalian cell contains between 10,000 and 30,000 different mRNA sequences (Davidson, Gene Activity in Early Development, 2nd ed., Academic Press, New York, 1976). The number of clones required to achieve a given probability that a low-abundance mRNA will be present in a cDNA library is $N=(\ln(1-P))/(\ln(1-1/n))$ where N is the number of clones required, P is the probability desired, and 1/n is the fractional proportion of the total mRNA that is represented by a single rare mRNA (Sambrook et al., 1989).

One method to enrich preparations of mRNA for sequences of interest is to fractionate by size. One such method is to fractionate by electrophoresis through an agarose gel (Pennica et al., Nature 301:214, 1983). Another method employs sucrose gradient centrifugation in the presence of an agent, such as methylmercuric hydroxide, that denatures secondary structure in RNA (Schweinfest et al., Proc. Natl. Acad. Sci. U.S.A. 79:4997-5000, 1982).

ESTs can be sequenced by a number of methods. Two basic methods can be used for DNA sequencing, the chain termination method (Sanger et al., Proc. Natl. Acad. Sci. U.S.A. 74: 5463, 1977) and the chemical degradation method (Maxam and Gilbert, Proc. Nat. Acad. Sci. U.S.A. 74: 560, 1977). Automation and advances in technology, such as the replacement of radioisotopes with fluorescence-based sequencing, have reduced the effort required to sequence DNA (Craxton, Methods, 2: 20, 1991; Ju et al., Proc. Natl. Acad. Sci. U.S.A. 92: 4347, 1995; Tabor and Richardson, Proc. Natl. Acad. Sci. U.S.A. 92: 6339, 1995). Automated sequencers are available from a number of manufacturers including Pharmacia Biotech, Inc., Piscataway, N.J. (Pharmacia ALF); LI-COR, Inc., Lincoln, Nebr. (LI-COR 4,000); and Millipore, Bedford, Mass. (Millipore BaseStation).

ESTs longer than 150 bp have been found to be useful for similarity searches and mapping (Adams et al., Science 252: 1651, 1991). EST sequences normally range from 150-450 bases. This is the length of sequence information that is routinely and reliably generated using single run sequence data. Typically, only single run sequence data is obtained from the cDNA library (Adams et al., Science 252:1651, 1991). Automated single run sequencing typically results in an approximately 2-3% error or base ambiguity rate (Boguski et al., Nature Genetics, 4:332, 1993).

EST databases have been constructed or partially constructed from, for example, *C. elegans* (McCombrie et al., Nature Genetics 1:124, 1992); human liver cell line HepG2 (Okubo et al., Nature Genetics 2:173, 1992); human brain RNA (Adams et al., Science 252:1651, 1991; Adams et al., Nature 355:632, 1992); *Arabidopsis*, (Newman et al., Plant Physiol. 106:1241, 1994); and rice (Kurata et al., Nature Genetics 8:365, 1994). The present invention uses ESTs from a number of cDNA libraries, prepared from wheat tissues preferably from glume, lemma or palea, as a tool for the identification of genes expressed in these target tissues, which then facilitates the isolation of 5' regulatory sequences such as promoters that regulate the genes. In addition also EST libraries from floral tissues of rice are required to help identify the gene specific homologue prior to promoter isolation as well as EST libraries from other tissues are required as background libraries.

The ESTs generated from sequencing a range of cDNA libraries are stored in a computer database and these "raw" ESTs are sorted in groups of contiguous ESTs, i.e. ESTs originating from homologous mRNA transcripts in a process known as clustering.

A "cluster" is a group of sequences that share an identity of at least 90% over any 100 base pair window. By aligning the members of a cluster and calculating the consensus, a single, representative sequence for the cluster may be derived.

Computer-based sequence analyses can be used to identify differentially expressed sequences including, but not limited to, those sequences expressed in one tissue compared with another tissue. For example, a different set of sequences can be found from cDNA isolated from root tissue versus leaf tissue. Accordingly, sequences can be compared from cDNA libraries prepared from plants grown under different environmental or physiological conditions. Once the preferred sequences are identified from the cDNA library of interest, the genomic clones can be isolated from a genomic library prepared from the plant tissue, and corresponding regulatory sequences including but not limited to 5' regulatory sequences can be identified and isolated.

In one preferred embodiment, expressed sequence tags (EST) sequences from a variety of cDNA libraries are catalogued in a sequence database. This database is used to identify promoter targets from a particular tissue of interest. The selection of expressed sequence tags for subsequent promoter isolation is reflective of the presence of one or more sequences among the representative ESTs from a random sampling of an individual cDNA library or a collection of cDNA libraries.

For example, the identification of regulatory sequences that direct the expression of transcripts in tissue of interest is conducted by identifying ESTs found in tissues of interest such as lemma, palea or glume, and absent or in lower abundance in other cDNA libraries in the database. The identified EST leads are then used to identify the operably linked regulatory sequences from genomic DNA sequences accordingly.

By abundance as used herein is meant the number of times a clone or cluster of clones appears in a library. The sequences that are enhanced or in high abundance in a specific tissue or organ that represent a target expression profile are identified in this manner and primers can be designed from the identified EST sequences. A PCR-based approach can be used to amplify flanking regions from a genomic library of the target plant of interest. A number of methods are known to those of skill in the art to amplify unknown DNA sequences adjacent to a core region of known sequence. Methods include but are not limited to inverse PCR (IPCR), vectorette PCR, Y-shaped PCR, and genome walking approaches.

In a preferred embodiment, genomic DNA ligated to an adaptor is subjected to a primary round of PCR amplification with a gene-specific primer and a primer that anneals to the adaptor sequence. The PCR product is next used as the template for a nested round of PCR amplification with a second gene-specific primer and second adaptor. The resulting fragments from the nested PCR reaction are then isolated, purified and subcloned into an appropriate vector. The fragments are sequenced, and the translational start sites can be identified when the EST is derived from a truncated cDNA. The fragments can be cloned into plant expression vectors as transcriptional or translational fusions with a reporter gene such as β-glucuronidase (GUS). The constructs can be tested in transient analyses, and subsequently the 5' regulatory regions are operably linked to other genes and regulatory sequences of interest in a suitable plant transformation vector and the transformed plants are analyzed for the expression of the gene(s) of interest, by any number of methods known to those of skill in the art.

Any plant can be selected for the identification of genes and regulatory sequences. Examples of suitable plant targets for the isolation of genes and regulatory sequences would include but are not limited to Acadia, alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lily, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf grasses, turnip, a vine, watermelon, wheat, yams, and zucchini. Particularly preferred plant targets would include corn, cotton, rice, rye, barley, sorghum, oats, soybean, and wheat, most preferably wheat.

Any method that allows a differential comparison between different types or classes of sequences can be used to isolate genes or regulatory sequences of interest. For example, in one differential screening approach, a cDNA library from mRNA isolated from a particular tissue can be prepared in a bacteriophage host using a commercially available cloning kit. The plaques are spread onto plates containing lawns of a bacterial host such as *E. coli* to generate bacteriophage plaques. About $10^5$-$10^6$ plaques can be lifted onto DNA-binding membranes. Duplicate membranes are probed using probes generated from mRNA from the target and non-target or background tissue. The probes are labeled to facilitate detection after hybridization and development. Plaques that hybridize to target tissue-derived probes but not to non-target tissue derived probes that display a desired differential pattern of expression can be selected for further analysis. Genomic DNA libraries can also be prepared from a chosen species by partial digestion with a restriction enzyme and size selecting the DNA fragments within a particular size range. The genomic DNA can be cloned into a suitable vector including but not limited to a bacteriophage and prepared using a suitable vector such as a bacteriophage using a suitable cloning kit from any number of vendors (see for example Stratagene, La Jolla Calif. or Gibco BRL, Gaithersburg, Md.).

Differential hybridization techniques as described are well known to those of skill in the art and can be used to isolate a desired class of sequences. By classes of sequences as used herein is meant sequences that can be grouped based on a common identifier including but not limited to sequences isolated from a common target plant, a common library, or a common plant tissue type. In a preferred embodiment, sequences of interest are identified based on sequence analyses and querying of a collection of diverse cDNA sequences from libraries of different tissue types. The disclosed method provides an example of a differential screening approach based on electronic sequence analyses of plant ESTs derived from diverse cDNA libraries.

A number of methods used to assess gene expression are based on measuring the mRNA level in an organ, tissue, or cell sample. Typical methods include but are not limited to RNA blots, ribonuclease protection assays and RT-PCR. In another preferred embodiment, a high-throughput method is used whereby regulatory sequences are identified from a transcript profiling approach. The development of cDNA microarray technology enables the systematic monitoring of gene expression profiles for thousands of genes (Schena et al, Science, 270: 467, 1995). This DNA chip-based technology arrays thousands of cDNA sequences on a support surface. These arrays are simultaneously hybridized to multiple labeled cDNA probes prepared from RNA samples of different cell or tissue types, allowing direct comparative analysis of expression. This technology was first demonstrated by analyzing 48 *Arabidopsis* genes for differential expression in roots and shoots (Schena et al, Science, 270:467, 1995). More recently, the expression profiles of over 1400 genes were monitored using cDNA microarrays (Ruan et al, The Plant Journal 15:821, 1998). Microarrays provide a high-throughput, quantitative and reproducible method to analyze gene expression and characterize gene function. The transcript profiling approach using microarrays thus provides another valuable tool for the isolation of regulatory sequences such as promoters associated with those genes.

The present invention uses high throughput sequence analyses to form the foundation of rapid computer-based identification of sequences of interest. Those of skill in the art are aware of the resources available for sequence analyses. Sequence comparisons can be done by determining the similarity of the test or query sequence with sequences in publicly available or proprietary databases ("similarity analysis") or by searching for certain motifs ("intrinsic sequence analysis") (e.g., cis elements) (Coulson, Trends in Biotechnology, 12:76, 1994; Birren et al., Genome Analysis, 1:543, 1997).

The nucleotide sequences provided in SEQ ID NOS: 1-3 or fragments thereof, or complements thereof, or a nucleotide sequence at least 90% identical, preferably 95% identical even more preferably 99% or 100% identical to the sequence provided in SEQ ID NOS: 1-3 or fragment thereof, or complement thereof, can be "provided" in a variety of mediums to facilitate use. Such a medium can also provide a subset thereof in a form that allows one of skill in the art to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable media can be used to create a manufacture comprising computer readable medium having recorded thereon a nucleotide sequence of the present invention.

By providing one or more of nucleotide sequences of the present invention, those of skill in the art can routinely access the sequence information for a variety of purposes. Computer software is publicly available that allows one of skill in the art to access sequence information provided in a computer readable medium. Examples of public databases would include but are not limited to the DNA Database of Japan (DDBJ); Genbank; and the European Molecular Biology Laboratory Nucleic Acid Sequence Database (EMBL) or versions thereof. A number of different search algorithms have been developed, including but not limited to the suite of programs referred to as BLAST programs. There are five implementations of BLAST, three designed for nucleotide sequence queries (BLASTN, BLASTX, and TBLASTX) and two designed for protein sequence queries (BLASTP and TBLASTN) (Coulson, Trends in Biotechnology, 12:76-80, 1994; Birren et al., Genome Analysis, 1:543, 1997).

Homologues in other organisms are available that can be used for comparative sequence analysis. Multiple alignments are performed to study similarities and differences in a group of related sequences. CLUSTAL W is a multiple sequence alignment package available that performs progressive multiple sequence alignments based on the method of Feng and Doolittle, *J. Mol. Evol.* 25: 351-360 (1987), the entirety of which is herein incorporated by reference. Each pair of sequences is aligned and the distance between each pair is calculated; from this distance matrix, a guide tree is calculated, and all of the sequences are progressively aligned based on this tree. A feature of the program is its sensitivity to the effect of gaps on the alignment; gap penalties are varied to encourage the insertion of gaps in probable loop regions instead of in the middle of structured regions. Users can specify gap penalties, choose between a number of scoring matrices, or supply their own scoring matrix for both the pairwise alignments and the multiple alignments. CLUSTAL W for UNIX and VMS systems is available at: ftp.ebi.ac.uk. Another program is MACAW (Schuler et al., *Proteins, Struct. Func. Genet,* 9:180-190 (1991), the entirety of which is herein incorporated by reference, for which both Macintosh and Microsoft Windows versions are available. MACAW uses a graphical interface, provides a choice of several alignment algorithms, and is available by anonymous ftp at: ncbi.nlm.nih.gov (directory/pub/macaw).

Any program designed for motif searching also has utility in the present invention. Sequence analysis programs designed for motif searching can be used for identification of cis elements. Preferred computer programs would include but are not limited to MEME, SIGNAL SCAN, and GENESCAN. MEME is a program that identifies conserved motifs (either nucleic acid or peptide) in a group of unaligned sequences. MEME saves these motifs as a set of profiles. These profiles can be used to search a database of sequences. A MEME algorithm was utilized in a previous study (Bailey and Elkan, Machine Learning, 21(1-2):51-80, 1995). SIGNALSCAN is a program that identifies known motifs in the test sequences using information from other motif databases (Prestridge, CABBIOS 7, 203-206, 1991). Databases used with SIGNALSCAN include PLACE (Higo et al., Nucleic Acids Research 27(1):297-300, 1999) and TRANSFAC (Heinemeye, X. et al., Nucleic Acid Research 27(1):318-322). GENESCAN is another suitable program for motif searching (Burge and Karlin, J. Mol. Biol. 268, 78-94, 1997). As used herein, "a target structural motif" or "target motif" refers any rationally selected BLASTN takes a nucleotide sequence (the query sequence) and its reverse complement and searches them against a nucleotide sequence database. BLASTN was designed for speed, not maximum sensitivity, and may not find distantly related coding sequences. BLASTX takes a nucleotide sequence, translates it in three forward reading frames and three reverse complement reading frames, and then compares the six translations against a protein sequence database. BLASTX is useful for sensitive analysis of preliminary (single-pass) sequence data and is tolerant of sequencing errors (Gish and States, *Nature Genetics,* 3: 266-272 (1993), herein incorporated by reference). BLASTN and BLASTX may be used in concert for analyzing EST data (Coulson, *Trends in Biotechnology,* 12: 76-80 (1994); Birren, et al., *Genome Analysis,* 1: 543-559 (1997)).

Given a coding nucleotide sequence and the protein it encodes, it is often preferable to use the protein as the query sequence to search a database because of the greatly increased sensitivity to detect more subtle relationships. This is due to the larger alphabet of proteins (20 amino acids) compared with the alphabet of nucleic acid sequences (4 bases), where it is far easier to obtain a match by chance. In addition; with nucleotide alignments, only a match (positive score) or a mismatch (negative score) is obtained, but with proteins, the presence of conservative amino acid substitutions can be taken into account. Here, a mismatch may yield a positive score if the non-identical residue has physical/chemical properties similar to the one it replaced. Various scoring matrices are used to supply the substitution scores of all possible amino acid pairs. A general purpose scoring system is the BLOSUM62 matrix (Henikoff and Henikoff, *Proteins,* 17: 49-61 (1993), herein incorporated by reference in its entirety), which is currently the default choice for BLAST programs. BLOSUM62 is tailored for alignments of moderately diverged sequences and thus may not yield the best results under all conditions. Altschul, *J. Mol. Biol.* 36: 290-300 (1993), herein incorporated by reference in its entirety, uses a combination of three matrices to cover all contingencies. This may improve sensitivity, but at the expense of slower searches. In practice, a single BLOSUM62 matrix is often used but others (PAM40 and PAM250) may be attempted when additional analysis is necessary. Low PAM matrices are directed at detecting very strong but localized sequence similarities, whereas high PAM matrices are directed at detecting long but weak alignments between very distantly related sequences. sequence or combination of sequences in which the sequence(s) are chosen based on a three-dimensional configuration that is formed upon the folding of the target motif. There are a variety of target motifs known to those of skill in the art. Protein target motifs include, but are not limited to, enzymatic active sites and signal sequences. Preferred target motifs of the present invention would include but are not limited to promoter sequences, cis elements, hairpin structures and other expression elements such as protein binding sequences.

As used herein, "search means" refers to one or more programs that are implemented on the computer-based system to compare a target sequence or target structural motif with the sequence information stored within the data storage means. Search means are used to identify fragments or regions of the sequences of the present invention that match a particular target sequence or target motif. Multiple sequences can also be compared in order to identify common regions or motifs that may be responsible for specific functions. For example, cis elements or sequence domains that confer a specific expression profile can be identified when multiple promoter regions of similar classes of promoters are aligned and analyzed by certain software packages.

The present invention further provides systems, particularly computer-based systems, that contain the sequence information described herein. As used herein, a "computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. Those of skill in the art can appreciate that any one of the available computer-based systems are suitable for use in the present invention.

In a preferred embodiment, the flanking sequences containing the 5' regulatory elements of the present invention are isolated using a genome-walking approach (Universal GenomeWalker™ Kit, CLONTECH Laboratories, Inc., Palo Alto, Calif.). In brief, the purified genomic DNA is subjected to a restriction enzyme digest that produces genomic DNA fragments with ends that are ligated with GenomeWalker™ adaptors. GenomeWalker™ primers are used along with gene specific primers in two consecutive PCR reactions (primary and nested PCR reactions) to produce PCR products containing the 5' regulatory sequences that are subsequently cloned and sequenced.

In addition to their use in modulating gene expression, the promoter sequences of the present invention also have utility as probes or primers in nucleic acid hybridization experiments. The nucleic acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure (see for example Sambrook et al., 1989, at 9.52-9.55 and 9.47-9.52, 9.56-9.58; Kanehisa, Nucl. Acids Res. 12:203-213, 1984; Wetmur and Davidson, J. Mol. Biol. 31:349-370, 1968). Appropriate stringency conditions that promote DNA hybridization are, for example, 6.0×sodium chloride/sodium citrate (SSC) at about 45° C., followed by a wash of 2.0×SSC at 50° C., and they are known to those skilled in the art or can be found in laboratory manuals including but not limited to Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. For example, hybridization using DNA or RNA probes or primers can be performed at 65° C. in 6×SSC, 0.5% SDS, 5× Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA fragments. Detection of DNA segments via hybridization is well-known to those of skill in the art. Thus depending on the application envisioned, one will desire to employ varying hybridization conditions to achieve varying degrees of selectivity of probe towards target sequence and the method of choice will depend on the desired results.

The nucleic acid sequences in SEQ ID NOS: 1-3 and any variants thereof, are capable of hybridizing to other nucleic acid sequences under appropriately selected conditions of stringency. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low stringency" conditions. Similarly, the molecules are said to be "complementary" if they can hybridize to one another with sufficient stability to permit them to remain annealed to one another under conventional "high stringency" conditions. Conventional stringency conditions are described by Sambrook et al. (Molecular Cloning, A Laboratory Manual, $2^{nd}$ Ed., Cold Spring Harbor Press, Cold Spring Harbor, N.Y., 1989), and by Haymes et al. (Nucleic Acid Hybridization, A Practical Approach, IRL Press, Washington, D.C., 1985).

In a preferred embodiment, the nucleic acid sequences SEQ ID NOS: 1-3 or a fragment, region, cis element, or oligomer of these sequences may be used in hybridization assays of other plant tissues to identify closely related or homologous genes and associated regulatory sequences. These include but are not limited to Southern or northern hybridization assays on any substrate including but not limited to an appropriately prepared plant tissue, cellulose, nylon, or combination filter, chip, or glass slide. Such methodologies are well known in the art and are available in a kit or preparation that can be supplied by commercial vendors.

Of course, nucleic acid fragments can also be obtained by other techniques such as by directly synthesizing the fragment by chemical means, as is commonly practiced by using an automated oligonucleotide synthesizer. Fragments can also be obtained by application of nucleic acid reproduction technology, such as the PCR™ (polymerase chain reaction) technology or by recombinant DNA techniques generally known to those of skill in the art of molecular biology. Regarding the amplification of a target nucleic-acid sequence (e.g., by PCR) using a particular amplification primer pair, "stringent PCR conditions" refer to conditions that permit the primer pair to hybridize only to the target nucleic-acid sequence to which a primer having the corresponding wild-type sequence (or its complement) would bind and preferably to produce a unique amplification product.

A fragment of a nucleic acid as used herein is a portion of the nucleic acid that is less than full-length. For example, for the present invention any length of nucleotide sequence that is less than the disclosed nucleotide sequences of SEQ ID NOS: 1-3 is considered to be a fragment. A fragment can also comprise at least a minimum length capable of hybridizing specifically with a native nucleic acid under stringent hybridization conditions as defined above. The length of such a minimal fragment is preferably at least 8 nucleotides, more preferably 15 nucleotides, even more preferably at least 20 nucleotides, and most preferably at least 30 nucleotides of a native nucleic acid sequence.

The nucleic acid sequences of the present invention can also be used as probes and primers. Nucleic acid probes and primers can be prepared based on a native gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to a target DNA or RNA sequence under high stringency hybridization conditions and hybridize specifically to a target native sequence of another species under lower stringency conditions. Preferably, probes and primers according to the present invention have complete sequence similarity with the native sequence, although probes differing from the native sequence and that retain the ability to hybridize to target native sequences may be designed by conventional methods. Methods for preparing and using probes and primers are described (see Sambrook et al., 1989; Ausubel et al., 1992, and Innis et al., 1990). PCR-primer pairs can be derived from a known sequence, for example, by using computer programs intended for that purpose such as Primer (Version 0.5, © 1991, Whitehead Institute for Biomedical Research, Cambridge, Mass.). Primers and probes based on the native promoter sequences disclosed herein can be used to confirm and, if necessary, to modify the disclosed sequences by conventional methods, e.g., by re-cloning and re-sequencing.

In another embodiment, the nucleotide sequences of the promoters disclosed herein can be modified. Those skilled in the art can create DNA molecules that have variations in the nucleotide sequence. The nucleotide sequences of the present invention as shown in SEQ ID NOS: 1-3 may be modified or altered to enhance their control characteristics. One preferred method of alteration of a nucleic acid sequence is to use PCR to modify selected nucleotides or regions of sequences. These methods are known to those of skill in the art. Sequences can be modified, for example by insertion, deletion or replacement of template sequences in a PCR-based DNA modification approach. "Variant" DNA molecules are DNA molecules containing changes in which one or more nucleotides of a native sequence is deleted, added, and/or substituted, preferably while substantially maintaining promoter function. In the case of a promoter fragment, "variant" DNA can include changes affecting the transcription of a minimal promoter to which it is operably linked. Variant DNA molecules can be produced, for example, by standard DNA mutagenesis techniques or by chemically synthesizing the variant DNA molecule or a portion thereof.

In another embodiment, the nucleotide sequences as shown in SEQ ID NOS: 1-3 include any length of said nucleotide sequences that are capable of regulating an operably linked DNA sequence. For example, the sequences as disclosed in SEQ ID NOS: 1-3 may be truncated or portions deleted and still be capable of regulating transcription of an operably linked DNA sequence. In a related embodiment, a cis element of the disclosed sequences may confer a particular specificity such as conferring enhanced expression of operably linked DNA sequences in certain tissues. Consequently, any sequence fragments, portions, or regions of the disclosed sequences of SEQ ID NOS: 1-3 can be used as regulatory sequences including but not limited to cis elements or motifs of the disclosed sequences. For example, one or more base pairs may be deleted from the 5' or 3' end of a promoter sequence to produce a "truncated" promoter. One or more base pairs can also be inserted, deleted; or substituted internally to a promoter sequence. Promoters can be constructed such that promoter fragments or elements are operably linked for example, by placing such a fragment upstream of a minimal promoter. A minimal or basal promoter is a piece of DNA that is capable of recruiting and binding the basal transcription machinery. One example of basal transcription machinery in eukaryotic cells is the RNA polymerase II complex and its accessory proteins. The enzymatic components of the basal transcription machinery are capable of initiating and elongating transcription of a given gene, utilizing a minimal or basal promoter. That is, there are not added cis-acting sequences in the promoter region that are capable of recruiting and binding transcription factors that modulate transcription, e.g., enhance, repress, render transcription hormone-dependent, etc. Substitutions, deletions, insertions or any combination thereof can be combined to produce a final construct.

Native or synthetic nucleic acids according to the present invention can be incorporated into recombinant nucleic acid constructs, typically DNA constructs, capable of introduction into and replication in a host cell. In one preferred embodiment, the nucleotide sequences of the present invention as shown in SEQ ID NOS: 1-3 or fragments, variants or derivatives thereof are incorporated into an expression vector cassette that includes the promoter regions of the present invention operably linked to a genetic component such as a selectable, screenable, or scorable marker gene. The disclosed nucleic acid sequences of the present invention are preferably operably linked to a genetic component such as a nucleic acid that confers a desirable characteristic associated with plant morphology, physiology, growth and development, yield, nutritional enhancement, disease such as *Fusarium* head blight disease, or pest resistance, environmental or chemical tolerance. These genetic components such as marker genes or agronomic genes of interest can function in the identification of a transformed plant cell or plant, or a produce a product of agronomic utility.

In a preferred embodiment, one genetic component produces a product that serves as a selection device and functions in a regenerable plant tissue to produce a compound that would confer upon the plant tissue resistance to an otherwise toxic compound. Genes of interest for use as a selectable, screenable, or scorable marker would include but are not limited to GUS (coding sequence for beta-glucuronidase), GFP (coding sequence for green fluorescent protein), LUX (coding gene for luciferase), antibiotic resistance marker genes, or herbicide tolerance genes. Examples of transposons and associated antibiotic resistance genes include the transposons Tn5 (bla), Tn5 (nptII), Tn7 (dhfr), penicillins, kanamycin (and neomycin, G418, bleomycin); methotrexate (and trimethoprim); chloramphenicol; and tetracycline.

Characteristics useful for selectable markers in plants have been outlined in a report on the use of microorganisms (Advisory Committee on Novel Foods and Processes, July 1994). These include stringent selection with minimum number of nontransformed tissues, large numbers of independent transformation events with no significant interference with the regeneration, application to a large number of species, and availability of an assay to score the tissues for presence of the marker.

A number of selectable marker genes are known in the art and several antibiotic resistance markers satisfy these criteria, including those resistant to kanamycin (nptII), hygromycin B (aph IV) and gentamycin (aac3 and aacC4). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil (Cell Culture and Somatic Cell Genetics of Plants, Vols. I-III, Laboratory Procedures and Their Applications Academic Press, New York, 1984). Particularly preferred selectable marker genes for use in the present invention would include genes that confer resistance to compounds such as antibiotics like kanamycin and herbicides like glyphosate (Della-Cioppa et al., Bio/Technology 5(6), 1987; U.S. Pat. No. 5,463,175; U.S. Pat. No. 5,633,435). Other selection devices can also be implemented and would still fall within the scope of the present invention.

For the practice of the present invention, conventional compositions and methods for preparing and using vectors and host cells are employed, as discussed, inter alia, in Sambrook et al., 1989. In a preferred embodiment, the host cell is a plant cell. A number of vectors suitable for stable transfection of plant cells or for the establishment of transgenic plants have been described in, e.g., Pouwels et al. (Cloning Vectors: A Laboratory Manual, 1985, supp. 1987); Weissbach and Weissbach (Methods for Plant Molecular Biology, Academic Press, 1989); Gelvin et al. (Plant Molecular Biology Manual, Kluwer Academic Publishers, 1990); and Croy (Plant Molecular Biology LabFax, BIOS Scientific Publishers, 1993). Plant expression vectors can include, for example, one or more cloned plant genes under the transcriptional control of 5' and 3' regulatory sequences. They can also include a selectable marker as described to select for host cells containing the expression vector. Such plant expression vectors also contain a promoter regulatory region (e.g., a regulatory region controlling inducible or constitutive, environmentally or developmentally regulated, or cell- or tissue-specific expression), a transcription initiation start site, a ribosome binding site, an RNA processing signal, a transcription termination site, and a polyadenylation signal. Other sequences of bacterial origin are also included to allow the vector to be cloned in a bacterial host. The vector will also typically contain a broad host range prokaryotic origin of replication. In a particularly preferred embodiment, the host cell is a plant cell and the plant expression vector comprises a promoter region as disclosed in SEQ ID NOS: 1-3, an operably linked transcribable sequence, and a transcription termination sequence. Other regulatory sequences envisioned as genetic components in an expression vector include, but is not limited to, non-translated leader sequence that can be coupled with the promoter. Plant expression vectors also can comprise additional sequences including but not limited to restriction enzyme sites that are useful for cloning purposes.

A number of promoters have utility for plant gene expression for any gene of interest including but not limited to selectable markers, scorable markers, genes for pest tolerance, disease tolerance, nutritional enhancements and any other gene that confers a desirable trait or characteristic. Examples of constitutive promoters useful for plant gene expression include, but are not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988); the octopine synthase promoter (Fromm et al., Plant Cell 1:977, 1989); and the figwort mosaic virus (FMV) promoter as described in U.S. Pat. No. 5,378,619.

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunI, Siebertz et al., Plant Cell 1:961, 1989); or (5) chemicals such as methyl jasmonate, salicylic acid, or safener. It may also be advantageous to employ (6) organ-specific promoters (e.g., Roshal et al., EMBO J. 6:1155, 1987; Schernthaner et al., EMBO J. 7:1249, 1988; Bustos et al., Plant Cell 1:839, 1989).

Plant expression vectors can include RNA processing signals, e.g., introns, which may be positioned upstream or downstream of a polypeptide-encoding sequence in the transgene. In addition, the expression vectors may include additional regulatory sequences from the 3'-untranslated region of plant genes (Thornburg et al., Proc. Natl. Acad. Sci. USA 84:744, 1987; An et al., Plant Cell 1:115, 1989), e.g., a 3' terminator region to increase mRNA stability of the mRNA, such as the PI-II terminator region of potato or the octopine or nopaline synthase 3' terminator regions. Five-end non-translated regions of a mRNA can play an important role in translation initiation and can also be a genetic component in a plant expression vector. For example, non-translated 5' leader sequences derived from heat shock protein genes have been demonstrated to enhance gene expression in plants (see, for example U.S. Pat. No. 5,362,865). These additional upstream and downstream regulatory sequences may be derived from a source that is native or heterologous with respect to the other elements present on the expression vector.

The promoter sequences of the present invention are used to control gene expression in monocotyledonous plant cells, more specifically in cereals and even more specifically in defined wheat cells. The disclosed promoter sequences are genetic components that are part of vectors used in plant transformation. The promoter sequences of the present invention can be used with any suitable plant transformation plasmid or vector containing a selectable or screenable marker and associated regulatory elements, as described, along with one or more nucleic acids expressed in a manner sufficient to confer a particular desirable trait. Examples of suitable structural genes of agronomic interest envisioned by the present invention would include but are not limited to one or more genes for insect tolerance such as a gene encoding a B.t endotoxin., pest tolerance such as genes for fungal disease control, more specifically for *Fusarium* head blight disease control, herbicide tolerance such as genes conferring glyphosate tolerance, and genes for quality improvements such as yield, physiology, fertilizer, growth, development, morphology or plant product(s).

The promoter sequences of the present invention can be used in wheat tissue to control gene expression involved in yield enhancement, anti-fungal and anti-microbial attack e.g. *Fusarium, Microdochium, Stagnospora* and *Blumeria*. The promoter sequences according to the invention may be used in controlling expression of those genes active against insecticidal damage to grain, normally leading to pre-harvest sprouting because moisture gets into the insect damaged grain. In addition the promoter sequences of the invention can be used in controlling expression of those genes having an impact on plant stress e.g. heat or water stress.

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev. 9:207, 1991). The RNA could also be a catalytic RNA molecule (i.e., a ribozyme) engineered to cleave a desired endogenous mRNA product (see for example, Gibson and Shillitoe, Mol. Biotech. 7:125, 1997). Thus, any gene that produces a protein or mRNA that expresses a phenotype or morphology change of interest is useful for the practice of the present invention.

In addition to regulatory elements or sequences located upstream (5') or within a DNA sequence, there are downstream (3') sequences that affect gene expression and thus the term regulatory sequence as used herein refers to any nucleotide sequence located upstream, within, or downstream to a DNA sequence that controls, mediates, or affects expression of a gene product in conjunction with the protein synthetic apparatus of the cell.

The promoter sequences of the present invention may be modified, for example for expression in other plant systems. In another approach, novel hybrid promoters can be designed or engineered by a number of methods. Many promoters contain upstream sequences that activate, enhance or define the strength and/or specificity of the promoter (Atchison, Ann. Rev. Cell Biol. 4:127, 1988). T-DNA genes, for example, contain "TATA" boxes defining the site of transcription initiation and other upstream elements located upstream of the transcription initiation site modulate transcription levels (Gelvin, In: Transgenic Plants, Kung and Us, eds, San Diego: Academic Press, pp. 49-87, 1988). Chimeric promoter combined a trimer of the octopine synthase (ocs) activator to the mannopine synthase (mas) activator plus promoter and reported an increase in expression of a reporter gene (Min Ni et al., The Plant Journal 7:661, 1995). The upstream regulatory sequences of the present invention can be used for the construction of such chimeric or hybrid promoters. Methods for construction of variant promoters of the present invention include but are not limited to combining control elements of different promoters or duplicating portions or regions of a promoter (see for example U.S. Pat. No. 5,110,732 and U.S. Pat. No. 5,097,025). Those of skill in the art are familiar with the standard resource materials that describe specific conditions and procedures for the construction, manipulation and isolation of macromolecules (e.g., DNA molecules, plasmids, etc.), generation of recombinant organisms and the screening and isolation of genes, (see for example Sambrook et al., Molecular Cloning: A Laboratory Manual, Cold Spring Harbor Press, 1989; Maliga et al., Methods in Plant Molecular Biology, Cold Spring Harbor Press, 1995; Birren et al., Genome Analysis: volume 1, Analyzing DNA, (1997), volume 2, Detecting Genes, (1998), volume 3, Cloning Systems, (1999) volume 4, Mapping Genomes, (1999), Cold Spring Harbor, N.Y.).

The promoter sequences of the present invention may be incorporated into an expression vector using screenable or scorable markers as described and tested in transient analyses that provide an indication of gene expression in stable plant systems. Methods of testing gene expression in transient assays are known to those of skill in the art. Transient expression of marker genes has been reported using a variety of plants, tissues and DNA delivery systems. For example, types of transient analyses can include but are not limited to direct gene delivery via electroporation or particle bombardment of tissues in any transient plant assay using any plant species of interest. Such transient systems would include but are not limited to protoplasts from suspension cultures in wheat (Zhou et al., Plant Cell Reports 12:612. 1993, electroporation of leaf protoplasts of wheat (Sethi et al., J. Crop Sci. 52: 152, 1983; electroporation of protoplast prepared from corn tissue (Sheen, The Plant Cell 3: 225, 1991), or particle bombardment of specific tissues of interest. The present invention encompasses the use of any transient expression system to evaluate regulatory sequences operatively linked to selected reporter genes, marker genes or agronomic genes of interest. Examples of plant tissues envisioned to test in transients via an appropriate delivery system would include, but are not limited to, leaf base tissues, callus, cotyledons, roots, endosperm, embryos, floral tissue, pollen, and epidermal tissue.

Any scorable or screenable marker can be used in a transient assay. Preferred marker genes for transient analyses of the promoters or 5' regulatory sequences of the present invention include a GUS gene or a GFP gene. The expression vectors containing the 5' regulatory sequences operably linked to a marker gene are delivered to the tissues and the tissues are analyzed by the appropriate mechanism, depending on the marker. The quantitative or qualitative analyses are used as a tool to evaluate the potential expression profile of the 5' regulatory sequences when operatively linked to genes of agronomic interest in stable plants. Ultimately, the 5' regulatory sequences of the present invention are directly incorporated into suitable plant transformation expression vectors comprising the 5' regulatory sequences operatively linked to a transcribable DNA sequence interest, transformed into plants and the stably transformed plants and progeny thereof analyzed for the desired expression profile conferred by the 5' regulatory sequences.

Those of skill in the art are aware of the vectors suitable for plant transformation. Suitable vectors would include but are not limited to disarmed Ti-plasmids for *Agrobacterium*-mediated methods. These vectors can contain a resistance marker, 1-2 T-DNA borders, and origins of replication for *E. coli* and *Agrobacterium* along with one or more genes of interest and associated regulatory regions. Those of skill in the art are aware that for *Agrobacterium*-mediated approaches a number of strains and methods are available. Such strains would include but are not limited to *Agrobacterium* strains C58, LBA4404, EHA101 and EHA105. Particularly preferred strains are *Agrobacterium tumefaciens* strains. Other DNA delivery systems for plant transformation are also known to those of skill in the art and include, but are not limited to, particle bombardment of selected plant tissues.

Exemplary nucleic acids that may be introduced by the methods encompassed by the present invention include, for example, DNA sequences or genes from another species, or even genes or sequences that originate with or are present in the same species but are incorporated into recipient cells by genetic engineering methods rather than classical reproduction or breeding techniques. However, the term exogenous is also intended to refer to genes that are not normally present in the cell being transformed, or perhaps simply not present in the form, structure, etc., as found in the transforming DNA segment or gene, or genes that are normally present yet which one desires, e.g., to have over-expressed. Thus, the term "exogenous" or alternatively "heterologous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

The plant transformation vectors containing the promoter sequences of the present invention may be introduced into plants by any plant transformation method. Several methods are available for introducing DNA sequences into plant cells and are well known in the art. Suitable methods include but are not limited to bacterial infection, binary bacterial artificial chromosome vectors, direct delivery of DNA (e.g. via PEG-mediated transformation, desiccation/inhibition-mediated DNA uptake, electroporation, agitation with silicon carbide fibers), and acceleration of DNA coated particles (reviewed in Potrykus, Ann. Rev. Plant Physiol. Plant Mol. Biol., 42: 205, 1991).

Methods for specifically transforming dicots primarily use *Agrobacterium tumefaciens*. For example, transgenic plants reported include but are not limited to cotton (U.S. Pat. No. 5,004,863; U.S. Pat. No. 5,159,135; U.S. Pat. No. 5,518,908, WO 97/43430), soybean (U.S. Pat. No. 5,569,834; U.S. Pat. No. 5,416,011; McCabe et al., Bio/Technology, 6:923, 1988; Christou et al., Plant Physiol., 87:671, 1988); *Brassica* (U.S. Pat. No. 5,463,174), and peanut (Cheng et al., Plant Cell Rep., 15: 653, 1996).

Similar methods have been reported in the transformation of monocots. Transformation and plant regeneration using these methods have been described for a number of crops including but not limited to asparagus (*Asparagus officinalis*; Bytebier et al., Proc. Natl. Acad. Sci. U.S.A., 84: 5345, 1987); barley (*Hordeum vulgarae*; Wan and Lemaux, Plant Physiol., 104: 37, 1994); maize (*Zea mays*; Rhodes et al., Science, 240: 204, 1988; Gordon-Kamm et al., Plant Cell, 2: 603, 1990; Fromm et al., Bio/Technology, 8: 833, 1990; Koziel et al., Bio/Technology, 11: 194, 1993); oats (*Avena sativa*; Somers et al., Bio/Technology, 10: 1589, 1992); orchardgrass (*Dactylis glomerata*; Horn et al., Plant Cell Rep., 7: 469, 1988); rice (*Oryza sativa*, including indica and japonica varieties, Toriyama et al., Bio/Technology, 6: 10, 1988; Zhang et al., Plant Cell Rep., 7: 379, 1988; Luo and Wu, Plant Mol. Biol. Rep., 6: 165, 1988; Zhang and Wu, Theor. Appl. Genet., 76: 835, 1988; Christou et al., Bio/Technology, 9: 957, 1991); sorghum (*Sorghum bicolor*; Casas et al., Proc. Natl. Acad. Sci. U.S.A., 90: 11212, 1993); sugar cane (*Saccharum* spp.; Bower and Birch, Plant J., 2: 409, 1992); tall fescue (*Festuca arundinacea*; Wang et al., Bio/Technology, 10: 691, 1992); turfgrass (*Agrostis palustris*; Zhong et al., Plant Cell Rep., 13: 1, 1993); wheat (*Triticum aestivum*; Vasil et al., Bio/Technology, 10: 667, 1992; Weeks et al., Plant Physiol., 102: 1077, 1993; Becker et al., Plant, J. 5: 299, 1994), and alfalfa (Masoud et al., Transgen. Res., 5: 313, 1996). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoter sequences of the present invention. Those of skill in the art are aware of the numerous methods available for the analysis of transformed plants. A variety of methods are used to assess gene expression and determine if the introduced gene(s) is integrated, functioning properly, and inherited as expected. For the present invention the promoters can be evaluated by determining the expression levels of genes to which the promoters are operatively linked. A preliminary assessment of promoter function can be determined by a transient assay method using reporter genes, but a more definitive promoter assessment can be determined from the analysis of stable plants. Methods for plant analysis include but are not limited to Southern blots or northern blots, PCR-based approaches, biochemical analyses, phenotypic screening methods, field evaluations, and immunodiagnostic assays.

The methods of the present invention including but not limited to cDNA library preparation, genomic library preparation, sequencing, sequence analyses, PCR technologies, vector construction, transient assays, and plant transformation methods are well known to those of skill in the art and are carried out using standard techniques or modifications thereof.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Plant Material, RNA Isolation and cDNA Library Construction

Tissue for the construction of the lemma/palea target library (LIB3399) is collected as follows. *Triticum aestivum* (var. *Bobwhite*) seed are germinated and grown in a growth chamber (humidity—65%, temperature/light cycle—16 h light [18° C.]/8 h dark [16° C.], light intensity –43kLux). Tissue harvest is carried out after approx. 8 weeks growth as plants reach stage 65 of the BBCH growth scale (jointly developed by German agricultural institutes) when 50% of anthers are extruded. Lemma and palea tissue is removed and placed immediately in liquid nitrogen with subsequent storage at –80° C.

Total RNA is purified from lemma and palea tissue using TRIZOL (Gibco BRL, Life Technologies, Gaithersburg, Md. U.S.A.), essentially as recommended by the manufacturer. Poly A+ RNA (mRNA) is purified using magnetic oligo dT beads as recommended by the manufacturer (DYNABEADS, Dynal Corporation, Lake Success, N.Y. U.S.A.).

Construction of plant cDNA libraries is well known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md. U.S.A.) was used, following the conditions suggested by the manufacturer. cDNA is synthesised, size selected using a SEPHACRYL column (500-2000 bp inclusive) and directionally cloned into pSPORT1 (GibcoBRL, Life Technologies, Gaithersburg, Md. U.S.A.).

The cDNA libraries are plated on LB agar containing the appropriate antibiotics for selection and incubated at 37° C. for a sufficient time to allow the growth of individual colonies. Single colonies are placed in individual wells of 96-well microtiter plates containing LB liquid including the selective antibiotics. The plates are incubated overnight at approximately 37° C. with gentle shaking to promote growth of the cultures. Plasmid DNA is isolated from each clone using QIAPREP plasmid isolation kits, using the conditions recommended by the manufacturer (Qiagen Inc., Santa Clara, Calif. U.S.A.).

The template plasmid DNA clones is sequenced by initiation from the 5' end of each cDNA clone, the resultant sequences are referred to as expressed sequence tags (ESTs). The template plasmid DNA clones is then sequenced. The cDNAs are sequenced using a commercially available sequencing kit, such as the ABI PRISM dRhodamine Terminator Cycle Sequencing Ready Reaction Kit with AmpliTaq® DNA Polymerase, under the conditions recommended by the manufacturer (PE Applied Biosystems, Foster City, Calif.).

A number of sequencing techniques are known in the art, including fluorescence-based sequencing methodologies. These methods have the detection, automation and instrumentation capability necessary for the analysis of large volumes of sequence data. Currently, the 377 DNA Sequencer (Perkin-Elmer Corp., Applied. Biosystems Div., Foster City, Calif.) allows the most rapid electrophoresis and data collection. With these types of automated systems, fluorescent dye-labeled sequence reaction products are detected and data entered directly into the computer, producing a chromatogram that is subsequently viewed, stored, and analyzed using the corresponding software programs. These methods are known to those of skill in the art and have been described and reviewed (Birren et al., *Genome Analysis: Analyzing DNA*, 1, Cold Spring Harbor, N.Y., the entirety of which is herein incorporated by reference).

Example 2

EST Clustering

The ESTs generated from sequencing a range of *T. asetivum* cDNA libraries are stored in a computer database. The 'raw' ESTs are sorted into groups of contiguous ESTs, i.e. ESTs originating from homologous mRNA transcripts, in a process known as clustering.

The clustering process consists of three main steps:

1. The libraries are screened for vector contamination and poor quality sequence.

2. The sequences are compared to each other. Those sequences that have 90% identity over a 100 base pair range are considered to be in the same "bin".

3. All of the sequences in each "bin" are aligned generating a consensus sequence known as an EST cluster sequence. The sequences in a "bin" that do not align are moved to a new bin.

The lemma and palea cDNA library (LIB3399) comprises 5856 clones each of which are sequenced to produce an EST. These ESTs are then clustered with other available ESTs from further *T. aestivum* cDNA libraries to produce a set of *T. aestivum* EST cluster sequences. Table 1 (in Appendix) shows the 40 most abundant EST cluster sequences in LIB3399. Abundance is expressed as target count (number of ESTs from LIB3399 comprising the cluster) and percentage abundance (target count as a percentage of total number of ESTs in LIB3399).

Example 3

Measuring Abundance of EST Clusters Using BLAST

BLAST (Basic Local Alignment Search Tool) is a set of similarity search programs designed to query DNA and protein sequence databases. The BLAST programs have been designed for speed, with a minimal sacrifice of sensitivity to distant sequence relationships. The scores assigned in a BLAST search have a well-defined statistical interpretation, making real matches easier to distinguish from random background hits. BLAST uses a heuristic algorithm which seeks local as opposed to global alignments and is therefore able to detect relationships among sequences which share only isolated regions of similarity (Altschul et. al. J. Mol. Biol. 215 (3): 403-410).

The number of ESTs originating from a particular library, that comprise a particular EST cluster, provides a measure of the abundance of the corresponding mRNA transcript in the tissue used to make the library.

The 96 most abundant EST clusters from LIB3399 were used as query sequences to search a range of cDNA libraries (see table 2 in Appendix) using the BLAST algorithm. The number of 'hits' with an E value $<=1\times10^{-7}$ and a bit score $>=100$ (using default parameters except threshold extension $>=100$) were collated for each cDNA library from which the number of 'hits' in each tissue type was calculated (see table 3 in Appendix).

EST clusters selected were those in which the total number of hits in stem, leaf, embryo, endosperm and root were <5. Thirty seven of the 96 EST clusters analysed met this criteria. These were further reduced to 30 EST clusters by selecting on the criteria of very low expression ($<=1$ hit) in stem, leaf, embryo, endosperm and root. However if some anther expression was evident a higher level of expression in stem, leaf, embryo, endosperm and root was tolerated ($<=5$ hits). See chart (FIG. 1 in Appendix) for comparison of expression pattern of 3 EST clusters (3849_1, 17859_1 and 88_3 respectively) with desired expression pattern and another 4 with undesirable expression pattern.

dix). The number of hits (E value $<=1\times10^{-7}$, bit score $>=100$ and threshold extension $>=100$) were collated for tissue type allowing comparison of the tissue type expression pattern. See table 5 (in Appendix) for summary of the 30 wheat EST clusters associated rice cDNA homolog and rice genomic DNA sequence.

Three rice cDNAs; 109_1.R2011: 618_3.R2011 and 5842_1.R2011 (named LP1, LP3 and LP4 respectively) showed preferential expression in rice panicle over leaf tissue. A more stringent analysis of the query/subject sequence alignment suggested these three cDNAs were even more preferentially abundant in the panicle libraries than suggested by the original search conditions (see Table 6 in Appendix).

Example 5

Identification and Cloning of Putative Promoter Regions

The 25 identified rice cDNA homolog sequences were used as query sequences against an *O. sativa* genomic DNA library to identify corresponding genomic DNA sequences (see summary table 5).

A BLASTX (all six nucleotide reading frames) search of GenPeptPRT database (publicly available protein sequence) was conducted with the three rice unigene cDNAs LP1, LP3 and LP4. 'Best hits' are shown below, cDNA/gDNA alignments follow table 6 in Appendix.

| ID | Wheat EST Cluster | Rice cDNA homolog | Rice BAC homologue | 'Best hit' annotation | |
|---|---|---|---|---|---|
| | | | | Accession | Description |
| LP1 | TRIAE-CLUSTER3849_1 | 109_1.R2011 | OSM13175 | AAC05507 | *O. sativa* 1-aminocyclopropane-1-carboxylate oxidase (ACO2) |
| LP3 | TRIAE-CLUSTER17859_1 | 618_3.R2011 | OSM118362 | CAA81481 | *O. sativa* S-adenosyl methionine synthetase (pRSAM-1) |
| LP4 | TRIAE-CLUSTER88_3 | 5842_1.R2011 | OSM12402 | CAA59800 | *Z. mays* mRNA for plasma membrane H+ ATPase. |

Example 4

Identification of Homologous Rice cDNAs and Expression Analysis

The 30 wheat EST clusters were then used as query sequences against an *O. sativa* unigene database (Clustered and assembled whole rice species EST data set as of Sep. 21, 2000 (seqVersionCollection—Oryza_sativa_Unigene20000921) Last updated: Oct. 19, 2000 11:55 AM) to search for homologous rice cDNAs. Rice cDNA homologs were found for 25 of the 30 wheat EST clusters (see table 5).

The 25 homologous rice cDNA sequences were then used as query sequences against a range of *O. sativa* panicle and leaf/vegetative tissue EST databases (see table 4 in Appen- The rice cDNA sequences were aligned with their corresponding rice genomic sequence, the rice genomic sequence was translated in the same frame as the cDNA frame that gave rise to the hits above. This enabled deduction of the position of the putative 'TATA' box and ATG translation start codon for each genomic sequence (see FIGS. 2, 3 and 4). Further evidence for the position of the translation start codon was gathered by comparing the amino-terminal amino acid sequence of other closely related protein sequences.

Nested pairs of oligonucleotide PCR primers were designed for each rice genomic DNA sequence. An 'outer' primary pair were designed using primer design computer software (PRIMERSELECT-DNAStar) to amplify a region from approximately 1700 bp upstream of the putative translation start codon to 200 bp downstream of the putative translation start codon. This pair of primers were used with a rice (Nipponbare) genomic DNA template to produce primary PCR products.

The 'inner' secondary pair of primers were designed manually. The forward primer either incorporated a SalI site or annealed to a region immediately upstream of a SalI site within the putative promoter, approximately 1500 bp upstream of the putative translation start codon. The reverse primer was designed to anneal to the region of the putative ATG translation start codon but in so doing destroy the ATG in the amplified product by a single base pair substitution. A NotI restriction site was also included immediately downstream of the destroyed ATG codon. The secondary pair of primers were used to PCR amplify the putative promoter using the primary PCR product as a template.

With this method approx. 1500 bp of each putative promoter, including nucleotides immediately upstream of the putative ATG translation start codon, were amplified and cloned into a suitable cloning vector using SalI and NotI restriction sites.

Example 6

Promoter Analysis in Plants

For stable plant transformation the 5' regulatory sequences are cloned into a plant transformation vector such as pMON-CAM1 shown (FIG. 5). This is a double border (right and left T-DNA borders) plant binary transformation vector and contains the following genetic components: RACT is the first intron from the rice actin gene; GUS is the coding region for the reporter gene β-glucoronidase; NOS is the 3' termination signal from the nopaline synthase gene; Spec/Strep is the coding region for spectinomycin and streptomycin resistance; ori-pUC and ori-V are origins of replication; NPTII is the coding region for kanamycin resistance; HSP70 is an intron from the maize heat shock protein 70 gene as described in U.S. Pat. No. 5,593,874 (herein incorporated by reference in its entirety) and U.S. Pat. No. 5,859,347 (herein incorporated by reference in its entirety); and CaMV35S is the promoter for the 35S RNA from Cauliflower Mosaic Virus containing a duplication of the −90 to −300 region.

The promoter is operably linked to the GUS reporter gene along with other regulatory sequences including, but not limited to, non-translated leaders and terminators as described above, and transformed into a target crop of interest via an appropriate delivery system such as Agrobacterium-mediated transformation (see, for example, U.S. Pat. No. 5,569,834, herein incorporated by reference in its entirety, U.S. Pat. No. 5,416,011, herein incorporated by reference in its entirety, U.S. Pat. No. 5,631,152, herein incorporated by reference in its entirety, U.S. Pat. No. 5,159,135, herein incorporated by reference in its entirety and U.S. Pat. No. 5,004,863, herein incorporated by reference in its entirety) or particle bombardment methods (see, for example, Patent Applns. WO 92/15675. WO 97/48814 and European Patent Appln. 586, 355, and U.S. Pat. Nos. 5,120,657, 5,503,998, 5,830,728 and 5,015,580, all of which are herein incorporated by reference in their entirety).

A large number of transformation and regeneration systems and methods are available and well known to those skilled in the art. The stably transformed plants and progeny are subsequently analyzed for expression of the gene in tissues of interest by any number of molecular, immunodiagnostic, biochemical, and/or field evaluation methods known to those skilled in the art.

Wheat plants transformed with various promoter reporter constructs were analyzed for GUS activity in the glume, lemma, palea and flag leaf respectively. The results obtained are shown in Table 7.

TABLE 7

Comparison of GUS activity in wheat plants transformed with various promoter reporter constructs.

| Promoter | Glume | Lemma | Palea | Flag Leaf |
|---|---|---|---|---|
| ScBV | ++++ | ++++ | ++++ | ++++ |
| LP1 | ++ | +++ | +++ | + |
| LP3 | ++ | ++ | +++ | + |
| LP4 | +++ | +++ | +++ | − |
| PER1 | − | − | − | − |

ScBV—promoter from Sugarcane badnavirus which drives constitutive expression (Tzafrir et. al. 1998 Plant. Mol. Biol. 38, 347). PER1— promoter of the *Hordeum vulgare* peroxiredoxin gene which is expressed in embryo and aleurone tissue (Stacy et. al. 1996 Plant. Mol. Biol. 31, 1205). For LP1, LP3 and LP4: see SEQ.ID.NO.1, SEQ.ID.NO.2 and SEQ.ID.NO.3 respectively.

Tissues were dissected from numerous plants for each construct and individually stained histochemically for GUS activity according to the protocol of Jefferson (1987, Plant. Mol. Biol. Rep. 5, 387). GUS activity was assessed by scoring the intensity of blue coloration by eye and assigning the following values:

−for undetectable, +for detectable, and ++for low, +++for medium and ++++for high.

LP4 was chosen for further analysis due to its superior expression pattern compared to LP1 and LP3. A LP4 GUS fusion reporter construct, without the RACT intron (=rice-actin intron) was constructed by subcloning the LP4 promoter into the SalI and SmaI sites of pMON-CAM2 (FIG. 6).

Wheat plants were transformed with the pMON-CAM2 LP4 construct and the plants grown alongside control plants transformed with LTP1:GUS (also constructed in pMON-CAM2) and ScBV:GUS promoter reporter constructs. Tissues were dissected from a number of plants for each construct (ScBV n=9, LP4 n=22 and LTP1 n=31) and individually stained and scored for GUS activity as described above.

An individual plant transformed with LP4 gave rise to the expression pattern shown below (table 8). The remaining LP4 plants had no detectable GUS expression in all tissues, as was the case for all plants transformed with the LTP1 promoter. The LP4 promoter gave expression specifically in glume tissue in wheat. Similar expression would be seen in the glume tissue of the male flower in corn; the female flower may have a vestigial glume but apparently this is less anatomically similar to the wheat glume than the male flower structure.

TABLE 8

Comparison of GUS activity in wheat plants transformed with various promoter reporter constructs.

| Promoter | Glume | Lemma | Palea | Anther | Stigma | Ovary | Rachis | Flag Leaf |
|---|---|---|---|---|---|---|---|---|
| ScBV | +++ | ++++ | ++++ | ++++ | ++++ | ++++ | ++++ | ++++ |
| LP4 | + | + | − | − | − | − | − | − |
| LTP1 | − | − | − | − | − | − | − | − |

ScBV - promoter from Sugarcane Badnavirus which drives constitutive expression (Tzafrir et. al. 1998 Plant. Mol. Biol. 38, 347).
LTP1 - lipid transfer protein 1 promoter of *Hordeum vulgare* which is expressed in the aleurone layer of developing and germinating seeds (Skriver et. al. 1992 Plant Mol. Biol. 18, 585). For LP4 see SEQ. ID. NO. 3.

APPENDIX

TABLE 1

Example of the 40 most abundant EST clusters in the *T. aestivum* lemma/palea library (LIB3399).

| Order | Cluster ID | Target count | Abundance % |
|---|---|---|---|
| 1 | >000330-TRIAE-CLUSTER3710 1 | 79 | 1.35 |
| 2 | >000330-TRIAE-CLUSTER6572 1 | 32 | 0.55 |
| 3 | >000330-TRIAE-CLUSTER17792 1 | 24 | 0.41 |
| 4 | >000330-TRIAE-CLUSTER17955 1 | 22 | 0.38 |
| 5 | >000330-TRIAE-CLUSTER3849 1 | 21 | 0.36 |
| 6 | >000330-TRIAE-CLUSTER17777 1 | 19 | 0.32 |
| 7 | >000330-TRIAE-CLUSTER279 1 | 19 | 0.32 |
| 8 | >000330-TRIAE-CLUSTER87 1 | 17 | 0.29 |
| 9 | >000330-TRIAE-CLUSTER6204 1 | 17 | 0.29 |
| 10 | >000330-TRIAE-CLUSTER5324 1 | 14 | 0.24 |
| 11 | >000330-TRIAE-CLUSTER6752 1 | 13 | 0.22 |
| 12 | >000330-TRIAE-CLUSTER3407 1 | 13 | 0.22 |
| 13 | >000330-TRIAE-CLUSTER17722 1 | 12 | 0.20 |
| 14 | >000330-TRIAE-CLUSTER409 1 | 12 | 0.20 |
| 15 | >000330-TRIAE-CLUSTER9478 1 | 11 | 0.19 |
| 16 | >000330-TRIAE-CLUSTER222 1 | 11 | 0.19 |
| 17 | >000330-TRIAE-CLUSTER6566 1 | 11 | 0.19 |
| 18 | >000330-TRIAE-CLUSTER82 1 | 11 | 0.19 |
| 19 | >000330-TRIAE-CLUSTER19354 1 | 10 | 0.17 |
| 20 | >000330-TRIAE-CLUSTER19285 1 | 9 | 0.15 |
| 21 | >000330-TRIAE-CLUSTER18098 1 | 9 | 0.15 |
| 22 | >000330-TRIAE-CLUSTER9892 1 | 9 | 0.15 |
| 23 | >000330-TRIAE-CLUSTER334 1 | 9 | 0.15 |
| 24 | >000330-TRIAE-CLUSTER8904 1 | 8 | 0.14 |
| 25 | >000330-TRIAE-CLUSTER18816 1 | 8 | 0.14 |
| 26 | >000330-TRIAE-CLUSTER365 2 | 8 | 0.14 |
| 27 | >000330-TRIAE-CLUSTER6574 1 | 8 | 0.14 |
| 28 | >000330-TRIAE-CLUSTER3866 1 | 8 | 0.14 |
| 29 | >000330-TRIAE-CLUSTER5436 1 | 8 | 0.14 |
| 30 | >000330-TRIAE-CLUSTER11373 1 | 7 | 0.12 |
| 31 | >000330-TRIAE-CLUSTER81 1 | 7 | 0.12 |
| 32 | >000330-TRIAE-CLUSTER5588 1 | 7 | 0.12 |
| 33 | >000330-TRIAE-CLUSTER5155 1 | 7 | 0.12 |
| 34 | >000330-TRIAE-CLUSTER17758 1 | 7 | 0.12 |
| 35 | >000330-TRIAE-CLUSTER17828 1 | 7 | 0.12 |
| 36 | >000330-TRIAE-CLUSTER18381 1 | 7 | 0.12 |
| 37 | >000330-TRIAE-CLUSTER18232 1 | 6 | 0.10 |
| 38 | >000330-TRIAE-CLUSTER17954 1 | 6 | 0.10 |
| 39 | >000330-TRIAE-CLUSTER11291 1 | 6 | 0.10 |
| 40 | >000330-TRIAE-CLUSTER86 1 | 6 | 0.10 |

TABLE 2 cDNA libraries searched with most abundant EST clusters of the *T. aestivum* lemma/palea library (LIB3399).

| Library ID | No. clones | Species | Tissue | Stage |
|---|---|---|---|---|
| LIB3224 | 1632 | *Triticum aestivum* | Root | Young |
| LIB3226 | 12480 | *Triticum aestivum* | Root | Young |
| LIB3280 | 5760 | *Triticum aestivum* | Anther | Split Boot |
| LIB3350 | 12672 | *Triticum aestivum* | Anther | Pre-anthesis, 1-2 cm spikes |
| LIB3351 | 8736 | *Triticum aestivum* | Anther | Pre-anthesis, 5 cm spikes |
| LIB3352 | 23040 | *Triticum aestivum* | Anther | Pre-anthesis, 7-8 cm spikes |
| LIB3399 | 5856 | *Triticum aestivum* | Lemma/palea | Anthesis - BBCH growth scale: 65 (about 50% of anthers were extruded) |
| LIB3400 | 5856 | *Triticum aestivum* | Glume | Anthesis - BBCH growth scale: 65 (about 50% of anthers were extruded) |
| LIB3908 | 2688 | *Triticum aestivum* | Stem | Pre-anthesis, split boot |
| LIB3910 | 2688 | *Triticum aestivum* | Leaves | Pre-split boot |
| SATMON014 | 4465 | *Zea mays* | Endosperm | 14-D.A.P |
| SATMON017 | 7472 | *Zea mays* | Embryo | 21-D.A.P |
| SATMON033 | 3634 | *Zea mays* | Embryo | 13-D.A.P |
| SATMON036 | 6250 | *Zea mays* | Endosperm | 22-D.A.P |

Searching was conducted using the BLAST algorithim with a stringency of E value $<= 1 \times 10^{-7}$, bit score $>= 100$ and threshold extension $>= 100$.

TABLE 3

Abundance of wheat EST clusters across a range of tissue types as measured by BLAST technique

| Wheat EST Cluster ID | Lemma/palea | | Glume | | Anther | | Stem | |
|---|---|---|---|---|---|---|---|---|
| | Hits | % | Hits | % | Hits | % | Hits | % |
| >000330-TRIAE-CLUSTER3710_1 | 60 | 1.02 | 44 | 0.75 | 1 | 0.00 | 17 | 0.63 |
| >000330-TRIAE-CLUSTER18727_1 | 47 | 0.80 | 54 | 0.92 | 4 | 0.01 | 23 | 0.86 |
| >000330-TRIAE-CLUSTER6572_1 | 37 | 0.63 | 35 | 0.60 | 5 | 0.01 | 7 | 0.26 |
| >000330-TRIAE-CLUSTER9478_1 | 33 | 0.56 | 31 | 0.53 | 6 | 0.01 | 1 | 0.04 |
| >000330-TRIAE-CLUSTER332_2 | 29 | 0.50 | 21 | 0.36 | 19 | 0.04 | 31 | 1.15 |
| >000330-TRIAE-CLUSTER17792_1 | 27 | 0.46 | 21 | 0.36 | 0 | 0.00 | 0 | 0.00 |
| >000330-TRIAE-CLUSTER17955_1 | 27 | 0.46 | 19 | 0.32 | 1 | 0.00 | 0 | 0.00 |
| >000330-TRIAE-CLUSTER17777_1 | 25 | 0.43 | 24 | 0.41 | 0 | 0.00 | 8 | 0.30 |
| >000330-TRIAE-CLUSTER6204_1 | 24 | 0.41 | 14 | 0.24 | 35 | 0.07 | 0 | 0.00 |
| >000330-TRIAE-CLUSTER3849_1 | 23 | 0.39 | 24 | 0.41 | 3 | 0.01 | 0 | 0.00 |
| >000330-TRIAE-CLUSTER5155_1 | 23 | 0.39 | 12 | 0.20 | 47 | 0.09 | 0 | 0.00 |
| >000330-TRIAE-CLUSTER279_1 | 22 | 0.38 | 11 | 0.19 | 20 | 0.04 | 0 | 0.00 |
| >000330-TRIAE-CLUSTER87_1 | 21 | 0.36 | 13 | 0.22 | 6 | 0.01 | 13 | 0.48 |
| >000330-TRIAE-CLUSTER19292_1 | 18 | 0.31 | 8 | 0.14 | 11 | 0.02 | 7 | 0.26 |
| >000330-TRIAE-CLUSTER3407_1 | 17 | 0.29 | 12 | 0.20 | 19 | 0.04 | 3 | 0.11 |
| >000330-TRIAE-CLUSTER17722_1 | 14 | 0.24 | 12 | 0.20 | 0 | 0.00 | 0 | 0.00 |
| >000330-TRIAE-CLUSTER19354_1 | 14 | 0.24 | 1 | 0.02 | 0 | 0.00 | 0 | 0.00 |
| >000330-TRIAE-CLUSTER409_1 | 14 | 0.24 | 9 | 0.15 | 4 | 0.01 | 4 | 0.15 |
| >000330-TRIAE-CLUSTER5324_1 | 14 | 0.24 | 10 | 0.17 | 7 | 0.01 | 3 | 0.11 |
| >000330-TRIAE-CLUSTER6566_1 | 14 | 0.24 | 12 | 0.20 | 6 | 0.01 | 19 | 0.71 |
| >000330-TRIAE-CLUSTER82_1 | 14 | 0.24 | 1 | 0.02 | 0 | 0.00 | 0 | 0.00 |
| >000330-TRIAE-CLUSTER334_1 | 13 | 0.22 | 10 | 0.17 | 71 | 0.14 | 2 | 0.07 |
| >000330-TRIAE-CLUSTER18816_1 | 12 | 0.20 | 12 | 0.20 | 0 | 0.00 | 0 | 0.00 |
| >000330-TRIAE-CLUSTER365_2 | 12 | 0.20 | 5 | 0.09 | 0 | 0.00 | 4 | 0.15 |
| >000330-TRIAE-CLUSTER222_1 | 11 | 0.19 | 37 | 0.63 | 0 | 0.00 | 21 | 0.78 |
| >000330-TRIAE-CLUSTER5588_1 | 11 | 0.19 | 6 | 0.10 | 16 | 0.03 | 8 | 0.30 |
| >000330-TRIAE-CLUSTER86_1 | 11 | 0.19 | 2 | 0.03 | 1 | 0.00 | 2 | 0.07 |
| >000330-TRIAE-CLUSTER9892_1 | 11 | 0.19 | 8 | 0.14 | 3 | 0.01 | 1 | 0.04 |
| >000330-TRIAE-CLUSTER17828_1 | 10 | 0.17 | 17 | 0.29 | 0 | 0.00 | 0 | 0.00 |
| >000330-TRIAE-CLUSTER18098_1 | 10 | 0.17 | 8 | 0.14 | 0 | 0.00 | 1 | 0.04 |
| >000330-TRIAE-CLUSTER19285_1 | 10 | 0.17 | 1 | 0.02 | 0 | 0.00 | 0 | 0.00 |
| >000330-TRIAE-CLUSTER6574_1 | 10 | 0.17 | 14 | 0.24 | 3 | 0.01 | 9 | 0.33 |
| >000330-TRIAE-CLUSTER3866_1 | 9 | 0.15 | 12 | 0.20 | 11 | 0.02 | 5 | 0.19 |
| >000330-TRIAE-CLUSTER5436_1 | 9 | 0.15 | 8 | 0.14 | 14 | 0.03 | 6 | 0.22 |
| >000330-TRIAE-CLUSTER216_2 | 9 | 0.15 | 10 | 0.17 | 98 | 0.20 | 10 | 0.37 |
| >000330-TRIAE-CLUSTER11373_1 | 8 | 0.14 | 4 | 0.07 | 6 | 0.01 | 5 | 0.19 |
| >000330-TRIAE-CLUSTER17758_1 | 8 | 0.14 | 1 | 0.02 | 0 | 0.00 | 0 | 0.00 |
| >000330-TRIAE-CLUSTER237_3 | 8 | 0.14 | 6 | 0.10 | 69 | 0.14 | 13 | 0.48 |
| >000330-TRIAE-CLUSTER5053_1 | 8 | 0.14 | 6 | 0.10 | 3 | 0.01 | 1 | 0.04 |
| >000330-TRIAE-CLUSTER6752_1 | 8 | 0.14 | 24 | 0.41 | 0 | 0.00 | 24 | 0.89 |
| >000330-TRIAE-CLUSTER81_1 | 8 | 0.14 | 11 | 0.19 | 4 | 0.01 | 9 | 0.33 |
| >000330-TRIAE-CLUSTER8904_1 | 8 | 0.14 | 7 | 0.12 | 4 | 0.01 | 3 | 0.11 |
| >000330-TRIAE-CLUSTER18081_1 | 8 | 0.14 | 6 | 0.10 | 0 | 0.00 | 0 | 0.00 |
| >000330-TRIAE-CLUSTER17869_1 | 7 | 0.12 | 5 | 0.09 | 0 | 0.00 | 14 | 0.52 |
| >000330-TRIAE-CLUSTER17954_1 | 7 | 0.12 | 4 | 0.07 | 0 | 0.00 | 0 | 0.00 |
| >000330-TRIAE-CLUSTER18381_1 | 7 | 0.12 | 1 | 0.02 | 0 | 0.00 | 0 | 0.00 |
| >000330-TRIAE-CLUSTER18169_1 | 7 | 0.12 | 2 | 0.03 | 0 | 0.00 | 0 | 0.00 |
| >000330-TRIAE-CLUSTER20825_1 | 7 | 0.12 | 1 | 0.02 | 0 | 0.00 | 0 | 0.00 |
| >000330-TRIAE-CLUSTER335_1 | 7 | 0.12 | 1 | 0.02 | 32 | 0.06 | 3 | 0.11 |
| >000330-TRIAE-CLUSTER4082_1 | 7 | 0.12 | 5 | 0.09 | 35 | 0.07 | 6 | 0.22 |
| >000330-TRIAE-CLUSTER4256_1 | 7 | 0.12 | 8 | 0.14 | 32 | 0.06 | 5 | 0.19 |
| >000330-TRIAE-CLUSTER5101_1 | 7 | 0.12 | 6 | 0.10 | 33 | 0.07 | 3 | 0.11 |
| >000330-TRIAE-CLUSTER74_1 | 7 | 0.12 | 3 | 0.05 | 10 | 0.02 | 0 | 0.00 |
| >000330-TRIAE-CLUSTER11291_1 | 6 | 0.10 | 5 | 0.09 | 2 | 0.00 | 0 | 0.00 |
| >000330-TRIAE-CLUSTER1550_1 | 6 | 0.10 | 13 | 0.22 | 3 | 0.01 | 40 | 1.49 |
| >000330-TRIAE-CLUSTER18232_1 | 6 | 0.10 | 5 | 0.09 | 0 | 0.00 | 0 | 0.00 |
| >000330-TRIAE-CLUSTER6534_1 | 6 | 0.10 | 5 | 0.09 | 3 | 0.01 | 11 | 0.41 |
| >000330-TRIAE-CLUSTER10930_1 | 6 | 0.10 | 6 | 0.10 | 2 | 0.00 | 0 | 0.00 |
| >000330-TRIAE-CLUSTER19162_1 | 6 | 0.10 | 2 | 0.03 | 0 | 0.00 | 0 | 0.00 |
| >000330-TRIAE-CLUSTER19414_1 | 6 | 0.10 | 6 | 0.10 | 0 | 0.00 | 0 | 0.00 |
| >000330-TRIAE-CLUSTER8025_1 | 6 | 0.10 | 0 | 0.00 | 5 | 0.01 | 2 | 0.07 |
| >000330-TRIAE-CLUSTER8880_1 | 6 | 0.10 | 3 | 0.05 | 2 | 0.00 | 0 | 0.00 |
| >000330-TRIAE-CLUSTER9521_1 | 6 | 0.10 | 9 | 0.15 | 4 | 0.01 | 14 | 0.52 |
| >000330-TRIAE-CLUSTER10954_1 | 5 | 0.09 | 2 | 0.03 | 2 | 0.00 | 2 | 0.07 |
| >000330-TRIAE-CLUSTER1619_1_ | 5 | 0.09 | 5 | 0.09 | 2 | 0.00 | 3 | 0.11 |
| >000330-TRIAE-CLUSTER17819_1 | 5 | 0.09 | 5 | 0.09 | 0 | 0.00 | 0 | 0.00 |
| >000330-TRIAE-CLUSTER17859_1 | 5 | 0.09 | 7 | 0.12 | 0 | 0.00 | 0 | 0.00 |
| >000330-TRIAE-CLUSTER21050_1 | 5 | 0.09 | 3 | 0.05 | 0 | 0.00 | 0 | 0.00 |
| >000330-TRIAE-CLUSTER3735_1 | 5 | 0.09 | 4 | 0.07 | 3 | 0.01 | 4 | 0.15 |
| >000330-TRIAE-CLUSTER385_1 | 5 | 0.09 | 1 | 0.02 | 2 | 0.00 | 8 | 0.30 |
| >000330-TRIAE-CLUSTER4192_1 | 5 | 0.09 | 0 | 0.00 | 19 | 0.04 | 0 | 0.00 |
| >000330-TRIAE-CLUSTER5220_2 | 5 | 0.09 | 3 | 0.05 | 2 | 0.00 | 1 | 0.04 |

TABLE 3-continued

Abundance of wheat EST clusters across a range of tissue types as measured by BLAST technique

| | | | | | | | | |
|---|---|---|---|---|---|---|---|---|
| >000330-TRIAE-CLUSTER5294_1 | 5 | 0.09 | 1 | 0.02 | 17 | 0.03 | 6 | 0.22 |
| >000330-TRIAE-CLUSTER5389_1 | 5 | 0.09 | 4 | 0.07 | 1 | 0.00 | 0 | 0.00 |
| >000330-TRIAE-CLUSTER539_2 | 5 | 0.09 | 8 | 0.14 | 28 | 0.06 | 6 | 0.22 |
| >000330-TRIAE-CLUSTER6311_1 | 5 | 0.09 | 2 | 0.03 | 11 | 0.02 | 8 | 0.30 |
| >000330-TRIAE-CLUSTER7378_1 | 5 | 0.09 | 1 | 0.02 | 5 | 0.01 | 1 | 0.04 |
| >000330-TRIAE-CLUSTER9352_1 | 5 | 0.09 | 2 | 0.03 | 1 | 0.00 | 0 | 0.00 |
| >000330-TRIAE-CLUSTER17708_1 | 4 | 0.07 | 8 | 0.14 | 0 | 0.00 | 16 | 0.60 |
| >000330-TRIAE-CLUSTER17850_1 | 4 | 0.07 | 14 | 0.24 | 0 | 0.00 | 2 | 0.07 |
| >000330-TRIAE-CLUSTER18160_1 | 4 | 0.07 | 1 | 0.02 | 0 | 0.00 | 0 | 0.00 |
| >000330-TRIAE-CLUSTER18226_1 | 4 | 0.07 | 5 | 0.09 | 0 | 0.00 | 0 | 0.00 |
| >000330-TRIAE-CLUSTER18284_1 | 4 | 0.07 | 2 | 0.03 | 0 | 0.00 | 0 | 0.00 |
| >000330-TRIAE-CLUSTER18568_1 | 4 | 0.07 | 1 | 0.02 | 0 | 0.00 | 0 | 0.00 |
| >000330-TRIAE-CLUSTER18640_1 | 4 | 0.07 | 15 | 0.26 | 0 | 0.00 | 0 | 0.00 |
| >000330-TRIAE-CLUSTER18876_1 | 4 | 0.07 | 4 | 0.07 | 0 | 0.00 | 0 | 0.00 |
| >000330-TRIAE-CLUSTER19216_1 | 4 | 0.07 | 0 | 0.00 | 0 | 0.00 | 1 | 0.04 |
| >000330-TRIAE-CLUSTER19722_1 | 4 | 0.07 | 1 | 0.02 | 0 | 0.00 | 0 | 0.00 |
| >000330-TRIAE-CLUSTER227_1 | 4 | 0.07 | 0 | 0.00 | 1 | 0.00 | 2 | 0.07 |
| >000330-TRIAE-CLUSTER3542_1 | 4 | 0.07 | 8 | 0.14 | 5 | 0.01 | 3 | 0.11 |
| >000330-TRIAE-CLUSTER476_1 | 4 | 0.07 | 0 | 0.00 | 0 | 0.00 | 0 | 0.00 |
| >000330-TRIAE-CLUSTER5173_1 | 4 | 0.07 | 3 | 0.05 | 5 | 0.01 | 1 | 0.04 |
| >000330-TRIAE-CLUSTER640_1 | 4 | 0.07 | 2 | 0.03 | 45 | 0.09 | 3 | 0.11 |
| >000330-TRIAE-CLUSTER7442_1 | 4 | 0.07 | 1 | 0.02 | 1 | 0.00 | 0 | 0.00 |
| >000330-TRIAE-CLUSTER7965_1 | 4 | 0.07 | 1 | 0.02 | 3 | 0.01 | 0 | 0.00 |
| >000330-TRIAE-CLUSTER88_3 | 4 | 0.07 | 0 | 0.00 | 2 | 0.00 | 0 | 0.00 |

| | Leaf | | Embryo | | Endosperm | | Root | |
|---|---|---|---|---|---|---|---|---|
| Wheat EST Cluster ID | Hits | % | Hits | % | Hits | % | Hits | % |
| >000330-TRIAE-CLUSTER3710 1 | 30 | 1.12 | 0 | 0.00 | 0 | 0.00 | 0 | 0.00 |
| >000330-TRIAE-CLUSTER18727_1 | 23 | 0.86 | 0 | 0.00 | 0 | 0.00 | 0 | 0.00 |
| >000330-TRIAE-CLUSTER6572 1 | 19 | 0.71 | 0 | 0.00 | 0 | 0.00 | 0 | 0.00 |
| >000330-TRIAE-CLUSTER9478 1 | 7 | 0.26 | 0 | 0.00 | 0 | 0.00 | 0 | 0.00 |
| >000330-TRIAE-CLUSTER332_2 | 48 | 1.79 | 0 | 0.00 | 1 | 0.01 | 0 | 0.00 |
| >000330-TRIAE-CLUSTER17792 1 | 0 | 0.00 | 0 | 0.00 | 0 | 0.00 | 0 | 0.00 |
| >000330-TRIAE-CLUSTER17955 1 | 9 | 0.33 | 0 | 0.00 | 0 | 0.00 | 0 | 0.00 |
| >000330-TRIAE-CLUSTER17777 1 | 44 | 1.64 | 1 | 0.01 | 0 | 0.00 | 1 | 0.01 |
| >000330-TRIAE-CLUSTER6204 1 | 0 | 0.00 | 33 | 0.30 | 41 | 0.38 | 2 | 0.01 |
| >000330-TRIAE-CLUSTER3849 1 | 1 | 0.04 | 0 | 0.00 | 0 | 0.00 | 0 | 0.00 |
| >000330-TRIAE-CLUSTER5155 1 | 0 | 0.00 | 23 | 0.21 | 42 | 0.39 | 4 | 0.03 |
| >000330-TRIAE-CLUSTER279 1 | 2 | 0.07 | 18 | 0.16 | 14 | 0.13 | 6 | 0.04 |
| >000330-TRIAE-CLUSTER87 1 | 17 | 0.63 | 0 | 0.00 | 0 | 0.00 | 0 | 0.00 |
| >000330-TRIAE-CLUSTER19292_1 | 5 | 0.19 | 0 | 0.00 | 0 | 0.00 | 0 | 0.00 |
| >000330-TRIAE-CLUSTER3407 1 | 2 | 0.07 | 25 | 0.23 | 2 | 0.02 | 5 | 0.04 |
| >000330-TRIAE-CLUSTER17722 1 | 0 | 0.00 | 0 | 0.00 | 0 | 0.00 | 0 | 0.00 |
| >000330-TRIAE-CLUSTER19354 1 | 0 | 0.00 | 0 | 0.00 | 0 | 0.00 | 0 | 0.00 |
| >000330-TRIAE-CLUSTER409 1 | 1 | 0.04 | 0 | 0.00 | 0 | 0.00 | 0 | 0.00 |
| >000330-TRIAE-CLUSTER5324 1 | 29 | 1.08 | 0 | 0.00 | 0 | 0.00 | 0 | 0.00 |
| >000330-TRIAE-CLUSTER6566 1 | 68 | 2.53 | 0 | 0.00 | 0 | 0.00 | 0 | 0.00 |
| >000330-TRIAE-CLUSTER82 1 | 6 | 0.22 | 0 | 0.00 | 0 | 0.00 | 0 | 0.00 |
| >000330-TRIAE-CLUSTER334 1 | 4 | 0.15 | 31 | 0.28 | 19 | 0.18 | 1 | 0.01 |
| >000330-TRIAE-CLUSTER18816 1 | 6 | 0.22 | 0 | 0.00 | 0 | 0.00 | 0 | 0.00 |
| >000330-TRIAE-CLUSTER365 2 | 2 | 0.07 | 3 | 0.03 | 1 | 0.01 | 0 | 0.00 |
| >000330-TRIAE-CLUSTER222 1 | 62 | 2.31 | 0 | 0.00 | 0 | 0.00 | 20 | 0.14 |
| >000330-TRIAE-CLUSTER5588 1 | 4 | 0.15 | 14 | 0.13 | 1 | 0.01 | 7 | 0.05 |
| >000330-TRIAE-CLUSTER86 1 | 9 | 0.33 | 0 | 0.00 | 0 | 0.00 | 0 | 0.00 |
| >000330-TRIAE-CLUSTER9892 1 | 2 | 0.07 | 0 | 0.00 | 0 | 0.00 | 0 | 0.00 |
| >000330-TRIAE-CLUSTER17828 1 | 0 | 0.00 | 0 | 0.00 | 0 | 0.00 | 0 | 0.00 |
| >000330-TRIAE-CLUSTER18098 1 | 2 | 0.07 | 0 | 0.00 | 0 | 0.00 | 0 | 0.00 |
| >000330-TRIAE-CLUSTER19285 1 | 0 | 0.00 | 0 | 0.00 | 0 | 0.00 | 0 | 0.00 |
| >000330-TRIAE-CLUSTER6574 1 | 22 | 0.82 | 0 | 0.00 | 0 | 0.00 | 0 | 0.00 |
| >000330-TRIAE-CLUSTER3866 1 | 4 | 0.15 | 7 | 0.06 | 2 | 0.02 | 2 | 0.01 |
| >000330-TRIAE-CLUSTER5436 1 | 0 | 0.00 | 6 | 0.05 | 8 | 0.07 | 2 | 0.01 |
| >000330-TRIAE-CLUSTER216_2 | 4 | 0.15 | 11 | 0.10 | 9 | 0.08 | 2 | 0.01 |
| >000330-TRIAE-CLUSTER11373 1 | 5 | 0.19 | 0 | 0.00 | 0 | 0.00 | 0 | 0.00 |
| >000330-TRIAE-CLUSTER17758 1 | 0 | 0.00 | 0 | 0.00 | 1 | 0.01 | 0 | 0.00 |
| >000330-TRIAE-CLUSTER237 3 | 4 | 0.15 | 18 | 0.16 | 23 | 0.21 | 10 | 0.07 |
| >000330-TRIAE-CLUSTER5053 1 | 12 | 0.45 | 1 | 0.01 | 0 | 0.00 | 0 | 0.00 |
| >000330-TRIAE-CLUSTER6752 1 | 93 | 3.46 | 0 | 0.00 | 0 | 0.00 | 0 | 0.00 |
| >000330-TRIAE-CLUSTER81 1 | 19 | 0.71 | 0 | 0.00 | 0 | 0.00 | 0 | 0.00 |
| >000330-TRIAE-CLUSTER8904 1 | 12 | 0.45 | 0 | 0.00 | 0 | 0.00 | 0 | 0.00 |
| >000330-TRIAE-CLUSTER18081_1 | 1 | 0.04 | 0 | 0.00 | 0 | 0.00 | 0 | 0.00 |
| >000330-TRIAE-CLUSTER17869 1 | 2 | 0.07 | 0 | 0.00 | 0 | 0.00 | 0 | 0.00 |
| >000330-TRIAE-CLUSTER17954 1 | 0 | 0.00 | 0 | 0.00 | 0 | 0.00 | 0 | 0.00 |
| >000330-TRIAE-CLUSTER18381 1 | 11 | 0.41 | 0 | 0.00 | 0 | 0.00 | 0 | 0.00 |
| >000330-TRIAE-CLUSTER18169_1 | 0 | 0.00 | 0 | 0.00 | 0 | 0.00 | 0 | 0.00 |
| >000330-TRIAE-CLUSTER20825_1 | 0 | 0.00 | 0 | 0.00 | 0 | 0.00 | 0 | 0.00 |

TABLE 3-continued

Abundance of wheat EST clusters across a range of tissue types as measured by BLAST technique

| | | | | | | | | |
|---|---|---|---|---|---|---|---|---|
| >000330-TRIAE-CLUSTER335_1 | 0 | 0.00 | 7 | 0.06 | 6 | 0.06 | 2 | 0.01 |
| >000330-TRIAE-CLUSTER4082_1 | 2 | 0.07 | 4 | 0.04 | 3 | 0.03 | 4 | 0.03 |
| >000330-TRIAE-CLUSTER4256_1 | 9 | 0.33 | 9 | 0.08 | 4 | 0.04 | 3 | 0.02 |
| >000330-TRIAE-CLUSTER5101_1 | 2 | 0.07 | 15 | 0.14 | 11 | 0.10 | 2 | 0.01 |
| >000330-TRIAE-CLUSTER74_1 | 3 | 0.11 | 20 | 0.18 | 24 | 0.22 | 0 | 0.00 |
| >000330-TRIAE-CLUSTER11291 1 | 0 | 0.00 | 0 | 0.00 | 0 | 0.00 | 0 | 0.00 |
| >000330-TRIAE-CLUSTER1550 1 | 3 | 0.11 | 0 | 0.00 | 0 | 0.00 | 3 | 0.02 |
| >000330-TRIAE-CLUSTER18232 1 | 6 | 0.22 | 0 | 0.00 | 0 | 0.00 | 0 | 0.00 |
| >000330-TRIAE-CLUSTER6534 1 | 20 | 0.74 | 0 | 0.00 | 0 | 0.00 | 0 | 0.00 |
| >000330-TRIAE-CLUSTER10930_1 | 1 | 0.04 | 0 | 0.00 | 1 | 0.01 | 0 | 0.00 |
| >000330-TRIAE-CLUSTER19162_1 | 0 | 0.00 | 1 | 0.01 | 0 | 0.00 | 0 | 0.00 |
| >000330-TRIAE-CLUSTER19414_1 | 1 | 0.04 | 0 | 0.00 | 0 | 0.00 | 0 | 0.00 |
| >000330-TRIAE-CLUSTER8025_1 | 2 | 0.07 | 2 | 0.02 | 0 | 0.00 | 0 | 0.00 |
| >000330-TRIAE-CLUSTER8880_1 | 0 | 0.00 | 2 | 0.02 | 0 | 0.00 | 0 | 0.00 |
| >000330-TRIAE-CLUSTER9521_1 | 13 | 0.48 | 0 | 0.00 | 1 | 0.01 | 0 | 0.00 |
| >000330-TRIAE-CLUSTER10954_1 | 4 | 0.15 | 2 | 0.02 | 0 | 0.00 | 0 | 0.00 |
| >000330-TRIAE-CLUSTER1619_1_ | 6 | 0.22 | 11 | 0.10 | 0 | 0.00 | 1 | 0.01 |
| >000330-TRIAE-CLUSTER17819_1 | 0 | 0.00 | 1 | 0.01 | 4 | 0.04 | 0 | 0.00 |
| >000330-TRIAE-CLUSTER17859_1 | 0 | 0.00 | 0 | 0.00 | 0 | 0.00 | 0 | 0.00 |
| >000330-TRIAE-CLUSTER21050_1 | 1 | 0.04 | 0 | 0.00 | 0 | 0.00 | 0 | 0.00 |
| >000330-TRIAE-CLUSTER3735_1 | 4 | 0.15 | 1 | 0.01 | 1 | 0.01 | 0 | 0.00 |
| >000330-TRIAE-CLUSTER385_1 | 6 | 0.22 | 3 | 0.03 | 1 | 0.01 | 0 | 0.00 |
| >000330-TRIAE-CLUSTER4192_1 | 0 | 0.00 | 25 | 0.23 | 25 | 0.23 | 1 | 0.01 |
| >000330-TRIAE-CLUSTER5220_2 | 2 | 0.07 | 0 | 0.00 | 0 | 0.00 | 0 | 0.00 |
| >000330-TRIAE-CLUSTER5294_1 | 0 | 0.00 | 17 | 0.15 | 11 | 0.10 | 2 | 0.01 |
| >000330-TRIAE-CLUSTER5389_1 | 3 | 0.11 | 0 | 0.00 | 1 | 0.01 | 0 | 0.00 |
| >000330-TRIAE-CLUSTER539_2 | 5 | 0.19 | 10 | 0.09 | 6 | 0.06 | 1 | 0.01 |
| >000330-TRIAE-CLUSTER6311_1 | 0 | 0.00 | 15 | 0.14 | 21 | 0.20 | 3 | 0.02 |
| >000330-TRIAE-CLUSTER7378_1 | 0 | 0.00 | 0 | 0.00 | 3 | 0.03 | 2 | 0.01 |
| >000330-TRIAE-CLUSTER9352_1 | 0 | 0.00 | 2 | 0.02 | 2 | 0.02 | 0 | 0.00 |
| >000330-TRIAE-CLUSTER17708_1 | 8 | 0.30 | 0 | 0.00 | 0 | 0.00 | 0 | 0.00 |
| >000330-TRIAE-CLUSTER17850_1 | 0 | 0.00 | 0 | 0.00 | 0 | 0.00 | 0 | 0.00 |
| >000330-TRIAE-CLUSTER18160_1 | 0 | 0.00 | 0 | 0.00 | 0 | 0.00 | 0 | 0.00 |
| >000330-TRIAE-CLUSTER18226_1 | 0 | 0.00 | 0 | 0.00 | 0 | 0.00 | 0 | 0.00 |
| >000330-TRIAE-CLUSTER18284_1 | 1 | 0.04 | 0 | 0.00 | 0 | 0.00 | 0 | 0.00 |
| >000330-TRIAE-CLUSTER18568_1 | 0 | 0.00 | 0 | 0.00 | 0 | 0.00 | 0 | 0.00 |
| >000330-TRIAE-CLUSTER18640_1 | 0 | 0.00 | 0 | 0.00 | 0 | 0.00 | 0 | 0.00 |
| >000330-TRIAE-CLUSTER18876_1 | 1 | 0.04 | 0 | 0.00 | 0 | 0.00 | 0 | 0.00 |
| >000330-TRIAE-CLUSTER19216_1 | 0 | 0.00 | 0 | 0.00 | 0 | 0.00 | 0 | 0.00 |
| >000330-TRIAE-CLUSTER19722_1 | 0 | 0.00 | 0 | 0.00 | 2 | 0.02 | 0 | 0.00 |
| >000330-TRIAE-CLUSTER227_1 | 0 | 0.00 | 0 | 0.00 | 0 | 0.00 | 2 | 0.01 |
| >000330-TRIAE-CLUSTER3542_1 | 13 | 0.48 | 12 | 0.11 | 1 | 0.01 | 0 | 0.00 |
| >000330-TRIAE-CLUSTER476_1 | 0 | 0.00 | 1 | 0.01 | 1 | 0.01 | 0 | 0.00 |
| >000330-TRIAE-CLUSTER5173_1 | 12 | 0.45 | 1 | 0.01 | 6 | 0.06 | 10 | 0.07 |
| >000330-TRIAE-CLUSTER640_1 | 0 | 0.00 | 15 | 0.14 | 5 | 0.05 | 2 | 0.01 |
| >000330-TRIAE-CLUSTER7442_1 | 1 | 0.04 | 0 | 0.00 | 0 | 0.00 | 0 | 0.00 |
| >000330-TRIAE-CLUSTER7965_1 | 0 | 0.00 | 0 | 0.00 | 1 | 0.01 | 0 | 0.00 |
| >000330-TRIAE-CLUSTER88_3 | 0 | 0.00 | 1 | 0.01 | 0 | 0.00 | 0 | 0.00 |

TABLE 4

Rice cDNA libraries searched with rice cDNA homologs.

| Library | Species | Tissue | Description | # clones |
|---|---|---|---|---|
| LIB3220 | *Oryza sativa* (Cypress) | Panicles | Panicles just cracking open and panicles with ¾ of the florets open. | 20227 |
| LIB3221 | *Oryza sativa* (M202) | Panicles | Panicles just cracking open and panicles with ¾ of the florets open. | 13705 |
| LIB3479 | *Oryza sativa* (nipponbare) | Panicle | Booting through hard dough Booting through hard dough. | 4733 |
| LIB3431 | *Oryza sativa* (nipponbare) | Leaf | Three to Five Leaf Stage. | 10040 |
| LIB3432 | *Oryza sativa* (nipponbare) | Leaf from 3 to 4 Tiller stage | Three to four tiller stage. | 9209 |
| LIB3474 | *Oryza sativa* (nipponbare) | Leaf | Booting to dough stage and stem at elongation stage. | 7897 |
| LIB4309 | *Oryza sativa* (nipponbare) | Vegetative shoot apices | Plants 29 DAP. | 7411 |

The total number of clones in panicle libraries is 38665, the total number of clones in leaf/vegetative shoot libraries is 34557.

TABLE 5

Summary table

| Wheat EST Cluster ID | Rice cDNA ID | Bit score | E-val | Target Count Panicle | Leaf | Rice gDNA ID | Bit score | E-val | 5' extension |
|---|---|---|---|---|---|---|---|---|---|
| >000330-TRIAE-CLUSTER17792_1 | None | NA | NA | NA | NA | NA | NA | NA | NA |
| >000330-TRIAE-CLUSTER3849_1 | 109__1.R2011 | 686 | 0 | 19 | 5 | OSM13175 | 1776 | 0 | >1500 |
| >000330-TRIAE-CLUSTER409_1 | 6586__1.R2011 | 664 | 0 | 8 | 3 | OSM140625 | 113 | 2.00E−23 | >1500 |
| >000330-TRIAE-CLUSTER17722_1 | 106__7.R2011 | 80 | 4.00E−14 | 2 | 48 | OSM148653 | 84 | 9.00E−15 | >1500 |
| >000330-TRIAE-CLUSTER19354_1 | None | NA | NA | NA | NA | NA | NA | NA | NA |
| >000330-TRIAE-CLUSTER9892_1 | 8064__1.R2011 | 833 | 0 | 11 | 39 | OSM133379 | 946 | 0 | >1500 |
| >000330-TRIAE-CLUSTER17828_1 | LIB3433-029-P1-K1-H12 | 74 | 9.00E−13 | 1 | 0 | OSM11448 | 375 | 1.00E−103 | >1500 |
| >000330-TRIAE-CLUSTER19285_1 | 35206__1.R2011 | 385 | 1.00E−106 | 1 | 6 | OSM13626 | 398 | 1.00E−109 | >1500 |
| >000330-TRIAE-CLUSTER17758_1 | AU083478 | 149 | 2.00E−35 | No hit | No hit | No hit | NA | NA | NA |
| >000330-TRIAE-CLUSTER18081_1 | 5260__1.R2011 | 519 | 1.00E−147 | 12 | 38 | OSM118250 | 400 | 1.00E−109 | >1500 |
| >000330-TRIAE-CLUSTER17954_1 | jC-osleLIB3474023g07b1 | 137 | 9.00E−32 | 0 | 1 | No hit | NA | NA | NA |
| >000330-TRIAE-CLUSTER18169_1 | 1013__1.R2011 | 323 | 5.00E−88 | 1 | 13 | OSM133379 | 1003 | 0 | 800 |
| >000330-TRIAE-CLUSTER20825_1 | None | NA | NA | NA | NA | NA | NA | NA | NA |
| >000330-TRIAE-CLUSTER11291_1 | 7425__2.R2011 | 428 | 1.00E−119 | 15 | 17 | OSM1591 | 1516 | 0 | >1500 |
| >000330-TRIAE-CLUSTER8880_1 | 5475__1.R2011 | 545 | 1.00E−154 | 6 | 2 | OSM15146 | 751 | 0 | >1500 |
| >000330-TRIAE-CLUSTER10930_1 | 10428__1.R2011 | 735 | 0 | 6 | 34 | OSM150046 | 357 | 1.00E−96 | >1500 |
| >000330-TRIAE-CLUSTER19162_1 | 5818__2.R2011 | 276 | 1.00E−73 | 3 | 4 | No hit | NA | NA | NA |
| >000330-TRIAE-CLUSTER19414_1 | 70927__1.R2011 | 127 | 5.00E−27 | 0 | 0 | OSM1372 | 797 | 0 | >1500 |
| >000330-TRIAE-CLUSTER17859_1 | 618__3.R2011 | 72 | 4.00E−12 | 37 | 13 | OSM118362 | 577 | 1.00E−163 | >1500 |
| >000330-TRIAE-CLUSTER21050_1 | 13087__1.R2011 | 228 | 2.00E−59 | 5 | 19 | OSM18841 | 890 | 0 | 1400 |
| >000330-TRIAE-CLUSTFR7965_1 | 208__3.R2011 | 676 | 0 | 4 | 4 | AC021892 | 569 | 1.00E−160 | >1500 |
| >000330-TRIAE-CLUSTER88__3 | 5842__1.R2011 | 1118 | 0 | 16 | 3 | OSM12402 | 1758 | 0 | >1500 |
| >000330-TRIAE-CLUSTER7442_1 | 12088__1.R2011 | 920 | 0 | 3 | 6 | OSM12692 | 714 | 0 | >1500 |
| >000330-TRIAE-CLUSTER18160_1 | 8179__1.R2011 | 80 | 1.00E−14 | 3 | 0 | No hit | NA | NA | NA |
| >000330-TRIAE-CLUSTER18226_1 | 55925__1.R2011 | 412 | 1.00E−114 | 0 | 2 | No hit | NA | NA | NA |
| >000330-TRIAE-CLUSTER18568_1 | None | NA | NA | NA | NA | NA | NA | NA | NA |
| >000330-TRIAE-CLUSTER18640_1 | None | NA | NA | NA | NA | NA | NA | NA | NA |
| >000330-TRIAE-CLUSTER19216_1 | 103294__1.R2011 | 131 | 4.00E−30 | 1 | 2 | OSM131139 | 353 | 7.00E−96 | >1500 |
| >000330-TRIAE-CLUSTER18284_1 | 36179__1.R2011 | 402 | 1.00E−111 | 2 | 4 | No hit | NA | NA | NA |
| >000330-TRIAE-CLUSTER18876_1 | LIB3431-038-P1-K1-C1 | 833 | 0 | 0 | 1 | No hit | NA | NA | NA |

TABLE 6

Preferential abundance of three rice cDNAs in panicle libraries.

| Wheat EST Cluster | Rice cDNA | Low-stringency Panicle | Leaf | Pan./Leaf ratio | High-stringency Panicle | Leaf | Pan./Leaf ratio |
|---|---|---|---|---|---|---|---|
| >000330-TRIAE-CLUSTER3849_1 | 109__1.R2011 | 0.049 (19) | 0.014 (5) | 3.40 | 0.028 (11) | 0.003 (1) | 9.83 |
| >000330-TRIAE-CLUSTER17859_1 | 618__3.R2011 | 0.096 (37) | 0.038 (13) | 2.54 | 0.070 (27) | 0.006 (2) | 12.07 |
| >000330-TRIAE-CLUSTER88__3 | 5842__1.R2011 | 0.041 (16) | 0.009 (3) | 4.77 | 0.031 (12) | 0.006 (2) | 5.36 |

Abundance expressed as a percentage (number of hits in brackets).

SEQUENCES 1, 2 and 3 as Described in the Application

```
>LP1 promoter sequence included<
TCGACCAGATCGACACGACAAGGAGGTTGAGGCAGATGTGGATCGAGGCGGCCTTCGTCGGGCCACCACTGCGGACGGGT      80   SEQ. ID. NO. 1

CGAGGTGGCCGTCGTCGAGCTGCTACTGCACAGGTTGACAACGACGATGAGCGACGGCTTGTAAATACATAGTACAATAT     160

GTACATGAGCAATCCAGGAGGCGACTCCACCAGGTCTGAACCACCTTCCTAGCTCACCACCTTGCCACCATCGGCAACGT     240

CACCCACCCACTTCCGATGCCTGCCCTCTCCTCTCCTCTCACATTCTTTTTCTTTCTCTCTGCCTAATACAGATATTT      320

TTCTTCTATGAATTCAATTCATATTTTCTCGATCCATAAACACTGACGGCAAGAGCGAGCTATCACAGACGACACTCTTG    400
```

-continued

```
CTCCATGTGGGCATCGGTTGGTGCCTAGAGAGCTGATTTGATAGGATGAGGTTGGTCGGTTTGTTTTGAACGTGGACTAA    480

TCAACGTGAAGCAGGGAAGCCTTTAGAGGAGGTTGGCTTGTTCGGTTTAGTAGGTGGTTATAGAGGTGGTATTGGCCGGA    560

CACAATGTACGGTTTTTTCCTAACAAACTAAGCACTGTATGTTTTTTTGCATAATGTATGGTTTGATATTTTTTTCTTA    640

AAATGTTATATCTTCTTTAATATAATAAATTGCCACACCCTTTTTAAAAAACCTGATATGTGTCCATAGGACCTAGCCAT    720

GTGAAGTCTACATTTGACAAATCAAATTGATCAGGTCTGGGCCAGGTGTACTATGCCCAAAATTCTGTCATCATCAAATC    800

CAAAAAGCAAGGAACAGTCTCTTATCGATCTGTAGTTCTCTACTTAATAGAGTTGATCACTTAGGTTAGGTATATAGAAT    880

AGTAACCACCACTACCATTATAGTATTACACTATAGTACTACTACATCACAAAGGCATTAGACATTAATTAGGAGTAAGA    960

GCAAATCTTGTGGAGAACCTTTTTGTGACTGTGTCGGGTAACCGGCATGAACTCAACCTGCGGCGTGCACAGGACACAGT   1040

GTGATCAGATCGGATAATCAGATTAGCAGCTTAGCTTAGCTTAGCTTGCTTACGTCCACACTACTTTACTCTCCGTTGGA   1120

CCAAATCACTAAACTTTGTCGTAAACTCGTACTACCTCCGTGCCATAATAAGTGTAGCCATAAGTTTCCGCGTCCAACTT   1200

TGATCGTCCGTCTTATTTGAAACTTTTTTATAATTAGTATTTTTGTTGTTATGAGATGATAAAACATGAATAGTACTTTA   1280

CTCGTGACTTATGTTTTAATTTTTTTAAAAAAATTTTCAAATAAGACGAACGGTTAAAGTTAGATGCGGAAAACCATGG   1360

CTGCACTTATTTTGAGATGTAGGAAGTAAGGCATACCGCACACCACGTCCTGGGGGTCAGGCAGTCAGCCTAGTGAAAAA   1440

GATAACTGTGCAAGCTAGCTTCTCGCTCTCGCGCCTATAAATTGGGCGCTCGCCGCCGGCCTCAGAGTGCACACACAGAC   1520

ACACAGACGCACTCACACACTCAGCTTAAGCGAGCGAGCGAGTGAACGAGAGAGAGAGACAGAGAGC               1587

>LP3 promoter sequence included<
GGCCGCGCCCACCCGCCTCCCGTGGTGAGGGGGGGCCTATAAATGGGCCGCGCGAGACCAAGGCCCATCTCGCCGTGCCC     80   SEQ. ID. NO. 2

GGTCGGATCTAATTAATTTACCTCCTCCACCTCCTCCTCCTCCCCCCGATCGGATCGGCCCGGCCCCTCCTCCTCCGCCG    160

CCGCCACCGCCGCCGCAGGTGAGCCGCCGATTCCCCTGTCCTCGTTGCTGGTAGTGTTGTCGCGTGTGTTGCTGCTGC     240

TGCTGCTGCTGTCCGGCTTCTCCCTTCATTCTTGCGGCTTGAAAAGGGAGAGGAGGGTTTTAGCGCTCTTGGTAGGA      360

TCAAGCTCTCAGGTTGGATCTGAGCTCGTGGTTGGTTGTCTTGCGGACGTATCATCGTGCCTAGATATTGATTTGTTTGT   400

GCTGGTTTGGGAGGGTTATAAGGAGGGTTTATTGCTTTTCTTTCGATCTTGTGGTATGGTAGATTTAGATGGGGTTTCTT   480

TGGTTGGATTTAGGTGTTGTAAGTCTTATTTTTGTCATGCTTGCTTATTATTATGGATGGAGATGGAGAGAGAAGCAGTA   560

GGATGACTTCCTTTTAGATGTTTAATACCTTGATGCTTATCAAACGGCTTGCTGATAAACAACATGCTAGAGCAGTGGTT   640

TTAGTGCTAGTATTATGTCTTTGGCTGTCAGCTCATTTGACTGTTCTGCGGTAGATTCGAGTCATCCCCTTGGTCTTGGG   720

AGTTGGAATTCTTATAAATGAACGGAAAATGGAAAAAAAAATTGATTGGTGCCACTTCAAAGTTAAATATGCCAAGACGA   800

ATTGATATGTTTCTGCTGTTGTTTTATGCTCTTGATTAGTTGATGCGCATGTTCAATGATTTATGATGTTTGTCTTTGTG   880

GAAAGATTACATGTAAAGAGTATAGTAGAACCCCTAAAAGCTAGCCAGCGATTTCGCTCTTTTTTTCAGGTCTCCATGAT   960

ATGTTTACCCCTAAAAGTGGTATATTTATGTGATAGTTACAATACATAGTGGCACCACGATTGATTATGCGTTTATGCTG  1040

ATTCCGGCAGAAAATTGTTAGATTCCTTGTGCTCTATACCTGCTTGTTGCGCTTGTAGAGAATATTACAAATACCTAACA  1120

CTTGCCCAAGGAACTTAGGAACTTAGTCAACTCTTTGTAGGGACAACTATTTTAGCCCAAAATTGTGGTCTTGTCAGGTG  1200

CCAACAAACAGCATCTTGGCGTACATAAGCTATATAGAGGATTAAAAGGAATGTTTTGTTCCTTGCTACTGTTTTTTTA   1280

ACCTGTTTACTCAGGACAAATTTTGTTGCATAAACCATTTGTTCTAGGGATCAGTATTGTCCTCTCAGTGTGTTATGTAA  1360

GCATTTCCAGAAATCAATTGTCGCTATCAGCTTCCCTCACATTAGCTATCACTTATACCCCTTTTTTTCTCATAGGCTCA  1440

CCATGTCCATTTTATTCATGATATTTCTTTGTCTAAAGTATGTGAAATACCATTTTATGCAGATAGGTTGAGC          1513

SEQ.ID.NO.3
>LP4 promoter sequence included<
TCGACGGAGACTTTCTCTTCCTATCTGCCCCTATATAAGTTTTTTTATTTTATGTATTTTTCATATAAAAAAGTGGAT      80

GCTGCTAGCAGCTAGGTGATGCTTCCGTCACCTGCAAATTGCTCGTTGAAACCGGCTTTATTCAAGTGAATTATTTGCCC   160
```

```
ATTATGTGCAGGGGATTAGAATAATGCTAGGGGATGGTAGTACAACGCTTGGTCGGCTCTTACCTCTTTGAGAGCAGCAG    240

GGTTCAGTTTGACACTTGCAATTTTATATGTAAACCCCCAAGAAAAAAAGGTTTAGTGGAACAGATGGGAAATAGCTGAA    320

CTGAGGCAGCTAGGCCTGCACTGGAACATCCCTGATGAACTATTTAATTTCTTTTAAATCCAGCAACTACACAGATACAA    400

TCATGTCTTGTAGATAATACTTCTATCGAACGGTACGCAGGTGCCATTTGGGCGAAAATAAGATAGTACTTCTAGAGCCG    480

GCCATTGTAAATTGAACAGGAACAACAAGTTTAGCGTTAGTTCATATTAAAGCCAAATTTTATCACATGGATACTTTGTA    560

AGAGCGAGTTTAATAGTATAGCCCACTATTAGCTCCAATTCATCTCTGGCCAATCTAATAGTCAATTCGTCATATAATAA    640

TTGCTTACTATACTATTAGTATATGGCTCCACCCATCATACATACATTTTGTCTTAGATTCCGTACTGCAGCTGACTACA    720

TATATGTAGCCCGTAGCTCTTATCTCTCATATTTTATTTTATTAAAATATGTTTGTAGCTGGATAATAGTCTGCTATTAT    800

ACCTGCTCTAAGTCTTAAAATATTTCGATTTAGTCTTCTACAGATATGAGTGTACGCGCGTGTTTATATGGGTAGGTGTA    880

CGTTCATACTGTGTTTGTAATTTAATCCACCATCGAGATCAGCTAGCTTCGTTCGTCCGTGAGCCGCACGATCCACATCC    960

ATCGGACGGTCCAGCTTGTAAAATGAATCTCACTACTCTACTCACTCCAGGCACAACACGGACGGTTCCCCACGGAGTTA   1040

AAAAACCACACACACACTGTACACACCCAAAGCCCGAAAACCCGTTATCTCTCCCGTGATGCGGCGTGGGGCCCACCACC   1120

ACACACCACCCCAAGTGGCTGACATCCACAGCTCCGTGGGCCCGGGTCCCACAGCCTCCCTTTCCCCTCCCCCTCCAAGA   1200

GTCAAATCTCCACCTCCCCCCTACGCCCACGGCCCACCGACACGTGGGCCCCACGACCCAGCCAGCCAGAGTCCCAGAAG   1280

TTAACGGGGGCACGCGAACAGAGAGGGGGGCCCCGCGCGGCGAGGTGGGGCCCAGTGCGGGTATGAAGCGGGGAGGCGCT   1360

ATATAGAGCGCACCCATCCTCCTCCCCCTTCCTCCCTCTCCTCTCCACTACTAATACCACCACCGCCGCGCCGGAGGTGG   1440

AAGACGGACGGGGTAGAGTTGGGGTCTCGCGGTGAGCCGATTCCTCTCTAGTGGTCGCGCCTGGTGTGTTCGCCGACGAC   1520

GCCGGCGTCGCGTCAGCCAAGGGTGGGC                                                    1548
```

---

The invention claimed is:

1. An isolated monocotyledonous regulatory sequence comprising SEQ ID NO:3.

2. The monocotyledonous regulatory sequence according to claim 1, wherein the sequence is part of a chimeric or hybrid promoter.

3. The monocotyledonous regulatory sequence according to claim 1, wherein the sequence further comprises a minimal CaMV (cauliflower mosaic virus) promoter or a rice actin promoter.

4. The monocotyledonous regulatory sequence according to claim 3, wherein the sequence further comprises said minimal CaMV 35S promoter.

5. A DNA construct comprising an isolated nucleic acid sequence comprising SEQ ID NO:3, wherein the nucleic acid sequence is operably linked to a transcribable DNA sequence and a 3' non-translated region.

6. A plant cell comprising the DNA construct according to claim 5.

7. A plant tissue comprising the plant cell according to claim 6.

8. A transgenic plant comprising the DNA construct according to claim 5.

9. A method of regulating transcription of a DNA sequence in a monocotyledonous plant tissue, said method comprising introducing the construct of claim 5 into a monocotyledonous plant tissue.

10. The method of claim 9, wherein said nucleic acid sequence further comprises a hybrid or chimeric promoter.

11. The method of claim 9, wherein the monocotyledonous plant tissue is wheat tissue.

12. The method of claim 9, wherein said nucleic acid sequence further comprises a minimal promoter.

13. A method of producing a transgenic plant, said method comprising introducing into a plant cell the DNA construct according to claim 5, and regenerating a transgenic plant from said plant cell.

14. The method of claim 11, wherein the wheat tissue is lemma, palea or glume tissue.

15. The method of claim 12, wherein the minimal promoter is a CaMV or rice actin minimal promoter.

16. The method of claim 13, wherein the plant cell is a wheat cell.

17. The monocotyledonous regulatory sequence according to claim 2, wherein the sequence consists of SEQ ID NO:3.

18. The method of claim 13, wherein the isolated nucleic acid sequence consists of SEQ ID NO:3.

* * * * *

SEQUENCE LISTING

```
<160> NUMBER OF SEQ ID NOS: 12

<210> SEQ ID NO 1
<211> LENGTH: 1587
<212> TYPE: DNA
<213> ORGANISM: Oryza sativa
<220> FEATURE:
<221> NAME/KEY: TATA_signal
<222> LOCATION: (1476)..(1479)

<400> SEQUENCE: 1
tcgaccagat cgacacgaca aggaggttga ggcagatgtg gatcgaggcg gccttcgtcg      60
ggccaccact gcggacgggt cgaggtggcc gtcgtcgagc tgctactgca caggttgaca     120
acgacgatga gcgacggctt gtaaatacat agtacaatat gtacatgagc aatccaggag     180
gcgactccac caggtctgaa ccaccttcct agctcaccac cttgccacca tcggcaacgt     240
cacccaccca cttccgatgc ctgccctctc ctctcctctc acattctttt tctttctctc     300
tctgcctaat acagatattt ttcttctatg aattcaattc atattttctc gatccataaa     360
cactgacggc aagagcgagc tatcacagac gacactcttg ctccatgtgg gcatcggttg     420
gtgcctagag agctgatttg ataggatgag gttggtcggt ttgttttgaa cgtggactaa     480
tcaacgtgaa gcagggaagc ctttagagga ggttggcttg ttcggtttag taggtggtta     540
tagaggtggt attggccgga cacaatgtac ggttttttcc taacaaacta agcactgtat     600 gttttttgc ataatgtatg gtttgatatt ttttttctta aaatgttata tcttctttaa      660
tataataaat tgccacaccc ttttaaaaa acctgatatg tgtccatagg acctagccat      720
gtgaagtcta catttgacaa atcaaattga tcaggtctgg gccaggtgta ctatgcccaa     780
```

```
aattctgtca tcatcaaatc caaaaagcaa ggaacagtct cttatcgatc tgtagttctc    840
tacttaatag agttgatcac ttaggttagg tatatagaat agtaaccacc actaccatta    900
tagtattaca ctatagtact actacatcac aaaggcatta gacattaatt aggagtaaga    960
gcaaatcttg tggagaacct ttttgtgact gtgtcgggta accggcatga actcaacctg   1020
cggcgtgcac aggacacagt gtgatcagat cggataatca gattagcagc ttagcttagc   1080
ttagcttgct tacgtccaca ctactttact ctccgttgga ccaaatcact aaactttgtc   1140
gtaaactcgt actacctccg tgccataata agtgtagcca taagtttccg cgtccaactt   1200
tgatcgtccg tcttatttga aactttttta taattagtat ttttgttgtt atgagatgat   1260
aaaacatgaa tagtacttta ctcgtgactt atgttttaa ttttttttaaa aaaattttca   1320 aataagacga acggttaaag ttagatgcgg aaaaccatgg ctgcacttat tttgagatgt   1380
aggaagtaag gcataccgca caccacgtcc tgggggtcag gcagtcagcc tagtgaaaaa   1440
gataactgtg caagctagct tctcgctctc gcgcctataa attgggcgct cgccgccggc   1500
ctcagagtgc acacacagac acacagacgc actcacacac tcagcttaag cgagcgagcg   1560
agtgaacgag agagagagac agagagc                                       1587
```

<210> SEQ ID NO 2
<211> LENGTH: 1513
<212> TYPE: DNA
<213> ORGANISM: Oryza sativa
<220> FEATURE:
<221> NAME/KEY: TATA_signal
<222> LOCATION: (1232)..(1235)

<400> SEQUENCE: 2

```
ggccgcgccc acccgcctcc cgtggtgagg gggggcctat aaatgggccg cgcgagacca     60
aggcccatct cgccgtgccc ggtcggatct aattaattta cctcctccac ctcctcctcc    120 tcccccgat cggatcggcc cggcccctcc tcctccgccg ccgccaccgc cgccgcaggt    180
gagccgccga ttcccctgtc ctcgttgctg gtagtgttgt cgcgtgtgtg ttgctgctgc    240
tgctgctgct gctgtccggc ttctcccttc attcttgcgg cttgaaaagg gagaggaggg    300
ttttagcgct cttggtagga tcaagctctc aggttggatc tgagctcgtg gttggttgtc    360
ttgcggacgt atcatcgtgc ctagatattg atttgtttgt gctggtttgg gagggttata    420
aggagggttt attgcttttc tttcgatctt gtggtatggt agatttagat ggggtttctt    480
tggttggatt taggtgttgt aagtcttatt tttgtcatgc ttgcttatta ttatggatgg    540
agatggagag agaagcagta ggatgacttc ctttttagatg tttaataccct tgatgcttat    600 caaacggctt gctgataaac aacatgctag agcagtggtt ttagtgctag tattatgtct    660
ttggctgtca gctcatttga ctgttctgcg gtagattcga gtcatcccct tggtcttggg    720
agttggaatt cttataaatg aacgaaaat ggaaaaaaaa attgattggt gccacttcaa    780
agttaaatat gccaagacga attgatatgt ttctgctgtt gttttatgct cttgattagt    840
tgatgcgcat gttcaatgat ttatgatgtt tgtctttgtg gaaagattac atgtaaagag    900
tatagtagaa cccctaaaag ctagccagcg atttcgctct ttttttcagg tctccatgat    960
atgtttaccc ctaaaagtgg tatatttatg tgatagttac aatacatagt ggcaccacga   1020
ttgattatgc gtttatgctg attccggcag aaaattgtta gattccttgt gctctatacc   1080
tgcttgttgc gcttgtagag aatattacaa atacctaaca cttgcccaag gaacttagga   1140
acttagtcaa ctctttgtag ggacaactat tttagcccaa aattgtggtc ttgtcaggtg   1200
```

```
ccaacaaaac agcatcttgg cgtacataag ctatatagag gattaaaagg aatgttttgt    1260
tccttgctac tgttttttta acctgtttac tcaggacaaa ttttgttgca taaaccattt    1320
gttctaggga tcagtattgt cctctcagtg tgttatgtaa gcatttccag aaatcaattg    1380
tcgctatcag cttccctcac attagctatc acttataccc cttttttttct cataggctca    1440 ccatgtccat tttattcatg atatttcttt gtctaaagta tgtgaaatac cattttatgc    1500
agataggttg agc                                                       1513

<210> SEQ ID NO 3
<211> LENGTH: 1548
<212> TYPE: DNA
<213> ORGANISM: Oryza sativa
<220> FEATURE:
<221> NAME/KEY: TATA_signal
<222> LOCATION: (1360)..(1363)

<400> SEQUENCE: 3
tcgacggaga ctttctcttc ctatctgccc ctatataagt ttttttttatt ttatgtattt    60 ttcatataaa aaaagtggat gctgctagca gctaggtgat gcttccgtca cctgcaaatt    120
gctcgttgaa accggcttta ttcaagtgaa ttatttgccc attatgtgca ggggattaga    180
ataatgctag gggatggtag tacaacgctt ggtcggctct tacctctttg agagcagcag    240
ggttcagttt gacacttgca attttatatg taaaccccca agaaaaaaag gtttagtgga    300
acagatggga aatagctgaa ctgaggcagc taggcctgca ctggaacatc cctgatgaac    360
tatttaattt cttttaaatc cagcaactac acagatacaa tcatgtcttg tagataatac    420
ttctatcgaa cggtacgcag gtgccatttg ggcgaaaata agatagtact tctagagccg    480
gccattgtaa attgaacagg aacaacaagt ttagcgttag ttcatattaa agccaaattt    540
tatcacatgg atactttgta agagcgagtt taatagtata gcccactatt agctccaatt    600
catctctggc caatctaata gtcaattcgt catataataa ttgcttacta tactattagt    660
atatggctcc acccatcata catacatttt gtcttagatt ccgtactgca gctgactaca    720
tatatgtagc ccgtagctct tatctctcat attttatttt attaaaatat gtttgtagct    780
ggataatagt ctgctattat acctgctcta agtcttaaaa tatttcgatt tagtcttcta    840
cagatatgag tgtacgcgcg tgtttatatg ggtaggtgta cgttcatact gtgtttgtaa    900
tttaatccac catcgagatc agctagcttc gttcgtccgt gagccgcacg atccacatcc    960
atcggacggt ccagcttgta aaatgaatct cactactcta ctcactccag gcacaacacg    1020
gacggttccc cacggagtta aaaaaccaca cacacactgt acacacccaa agcccgaaaa    1080
cccgttatct ctcccgtgat gcggcgtggg gcccaccacc acacaccacc caagtggct     1140 gacatccaca gctccgtggg cccgggtccc acagcctccc tttccctcc ccctccaaga     1200 gtcaaatctc cacctccccc ctacgcccac ggccaccga cacgtgggcc ccacgaccca     1260
gccagccaga gtcccagaag ttaacggggg cacgcgaaca gagagggggg cccgcgcgg     1320 cgaggtgggg cccagtgcgg gtatgaagcg gggaggcgct atatagagcg cacccatcct    1380
cctccccctt cctccctctc ctccacta ctaataccac caccgccgcg ccggaggtgg      1440
aagacggacg gggtagagtt gggtctcgc ggtgagccga ttcctctcta gtggtcgcgc     1500
ctggtgtgtt cgccgacgac gccggcgtcg cgtcagccaa gggtgggc                 1548

<210> SEQ ID NO 4
<211> LENGTH: 320
```

```
<212> TYPE: DNA
<213> ORGANISM: Oryza sativa

<400> SEQUENCE: 4
ctagtgaaaa agataactgt gcaagctagc ttctcgctct cgcgcctata aattgggcgc      60
tcgccgccgg cctcagagtg cacacacaga cacacagacg cactcacaca ctcagcttaa     120
gcgagcgagc gagtgaacga gagagagaga cagagatggc gagtgttgcc tccttcccgg     180
tgatcaacat ggagaacctg gagaccgagg aggggcgc agcaatggag gtcatccgcg       240
acgcctgcga gaactggggc ttcttcgagg tgcatatgca tgccaagcac tagcatgtac     300
taaccagcaa aaaatgtta                                                  320

<210> SEQ ID NO 5
<211> LENGTH: 178
<212> TYPE: DNA
<213> ORGANISM: Oryza sativa

<400> SEQUENCE: 5
acacagacgc actcacacac tcagcttaag cgagcgagcg agtgaacgag agagagagac      60
agagatggcg agtgttgcct ccttcccggt gatcaacatg gagaacctgg agaccgagga     120
gagggcgca gcaatggagg tcatccgcga cgcctgcgag aactggggct tcttcgag       178

<210> SEQ ID NO 6
<211> LENGTH: 38
<212> TYPE: PRT
<213> ORGANISM: Oryza sativa

<400> SEQUENCE: 6

Met Ala Ser Val Ala Ser Phe Pro Val Ile Asn Met Glu Asn Leu Glu
 1               5                  10                  15
Thr Glu Glu Arg Gly Ala Ala Met Glu Val Ile Arg Asp Ala Cys Glu
             20                  25                  30
Asn Trp Gly Phe Phe Glu
         35

<210> SEQ ID NO 7
<211> LENGTH: 560
<212> TYPE: DNA
<213> ORGANISM: Oryza sativa

<400> SEQUENCE: 7
cttgtcaggt gccaacaaaa cagcatcttg gcgtacataa gctatataga ggattaaaag      60
gaatgttttg ttccttgcta ctgttttttt aacctgttta ctcaggacaa attttgttgc     120
ataaccatt tgttctaggg atcagtattg tcctctcagt gtgttatgta agcatttcca      180
gaaatcaatt gtcgctatca gcttccctca cattagctat cacttatacc cctttttttc     240
tcataggctc accatgtcca ttttattcat gatatttctt tgtctaaagt atgtgaaata     300
ccattttatg cagataggag aagatggccg cacttgatac cttcctcttt acctcggagt     360
ctgtgaacga gggccaccct gacaagctct gcgaccaagt ctcagatgct gtgcttgatg     420
cctgcctcgc cgaggaccct gacagcaagg tcgcttgtga cctgcacc aagacaaaca      480
tggtcatggt ctttggtgag atcaccacca aggctaacgt tgactatgag aagattgtca     540
gggagacatg ccgtaacatc                                                 560

<210> SEQ ID NO 8
<211> LENGTH: 158
```

```
<212> TYPE: DNA
<213> ORGANISM: Oryza sativa

<400> SEQUENCE: 8
cagatgctgt gcttgatgcc tgcctcgccg aggaccctga cagcaaggtc gcttgtgaga      60
cctgcaccaa gacaaacatg gtcatggtct ttggtgagat caccaccaag gctaacgttg     120
actatgagaa gattgtcagg gagacatgcc gtaacatc                             158

<210> SEQ ID NO 9
<211> LENGTH: 79
<212> TYPE: PRT
<213> ORGANISM: Oryza sativa

<400> SEQUENCE: 9

Met Ala Ala Leu Asp Thr Phe Leu Phe Thr Ser Glu Ser Val Asn Glu
1               5                   10                  15

Gly His Pro Asp Lys Leu Cys Asp Gln Val Ser Asp Ala Val Leu Asp
                20                  25                  30

Ala Cys Leu Ala Glu Asp Pro Asp Ser Lys Val Ala Cys Glu Thr Cys
            35                  40                  45

Thr Lys Thr Asn Met Val Met Val Phe Gly Glu Ile Thr Thr Lys Ala
        50                  55                  60

Asn Val Asp Tyr Glu Lys Ile Val Arg Glu Thr Cys Arg Asn Ile
65                  70                  75

<210> SEQ ID NO 10
<211> LENGTH: 320
<212> TYPE: DNA
<213> ORGANISM: Oryza sativa

<400> SEQUENCE: 10
gaggtggggc ccagtgcggg tatgaagcgg ggaggcgcta tatagagcgc acccatcctc      60 ctccccttc  ctccctctcc tctccactac taataccacc accgccgcgc cggaggtgga     120
agacggacgg ggtagagttg gggtctcgcg gtgagccgat tcctctctag tggtcgcgcc     180
tggtgtgttc gccgacgacg ccggcgtcgc gtcagccatg ggtgggctcg aggagatcaa     240
gaatgaggcc gttgatctgg tgagaaaatc actcgccgcc accagctacc tactacttct     300
tcttcctcgc ttcctccctc                                                 320

<210> SEQ ID NO 11
<211> LENGTH: 180
<212> TYPE: DNA
<213> ORGANISM: Oryza sativa

<400> SEQUENCE: 11
tctccactac taataccacc accgccgcgc cggaggtgga agacggacgg ggtagagttg      60
gggtctcgcg gtgagccgat tcctctctag tggtcgcgcc tggtgtgttc gccgacgacg     120
ccggcgtcgc gtcagccatg ggtgggctcg aggagatcaa gaatgaggcc gttgatctgg     180

<210> SEQ ID NO 12
<211> LENGTH: 14
<212> TYPE: PRT
<213> ORGANISM: Oryza sativa

<400> SEQUENCE: 12

Met Gly Gly Leu Glu Glu Ile Lys Asn Glu Ala Val Asp Leu
1               5                   10
```